(12) United States Patent
Tanaka

(10) Patent No.: US 10,149,642 B2
(45) Date of Patent: Dec. 11, 2018

(54) BODILY FLUID-COMPONENT ANALYZING APPARATUS

(71) Applicant: OMRON HEALTHCARE Co., Ltd., Kyoto (JP)

(72) Inventor: Shinya Tanaka, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 241 days.

(21) Appl. No.: 15/168,692

(22) Filed: May 31, 2016

(65) Prior Publication Data

US 2016/0345884 A1 Dec. 1, 2016

(30) Foreign Application Priority Data

Jun. 1, 2015 (JP) ................................. 2015-111365

(51) Int. Cl.
*A61B 5/15* (2006.01)
*A61B 5/151* (2006.01)
*A61B 5/157* (2006.01)

(52) U.S. Cl.
CPC .......... *A61B 5/1513* (2013.01); *A61B 5/1519* (2013.01); *A61B 5/150022* (2013.01); *A61B 5/15113* (2013.01); *A61B 5/150259* (2013.01); *A61B 5/150358* (2013.01); *A61B 5/157* (2013.01); *A61B 5/150061* (2013.01); *A61B 5/150068* (2013.01); *A61B 2562/0295* (2013.01)

(58) Field of Classification Search
CPC . A61B 5/15; A61B 5/15103; A61B 5/150022; A61B 5/150358; A61B 5/15115; A61B 5/1513; A61B 5/157; A61B 5/15186; A61B 5/150068; A61B 5/150061; A61B 2562/0295

See application file for complete search history.

(56) References Cited

U.S. PATENT DOCUMENTS 8,079,961 B2 * 12/2011 Saikley ................ A61B 5/1411
600/573
2010/0185118 A1 * 7/2010 Takashima ....... A61B 5/150022
600/583

FOREIGN PATENT DOCUMENTS

JP 2005205096 A 8/2005

* cited by examiner

*Primary Examiner* — Devin B Henson
(74) *Attorney, Agent, or Firm* — Maier & Maier, PLLC

(57) ABSTRACT

An integrated bodily-fluid-component analyzing apparatus includes a main body, a lancet holder connected to the main body so as to be movable back and forth along a predetermined movement path, a lancet removably attached to the lancet holder, and a test strip that is removably attached to the main body and is used to measure a component of the bodily fluid flowing from a pricked site of the living body pricked with the lancet. The movement path of the lancet holder and a bodily fluid inlet of the test strip face a specific position that is in a vicinity of the main body and at which the pricked site is to be placed. The apparatus further includes a pressing section that presses a portion of the living body adjacent to the pricked site so as to cause the bodily fluid to flow from the pricked site.

11 Claims, 20 Drawing Sheets

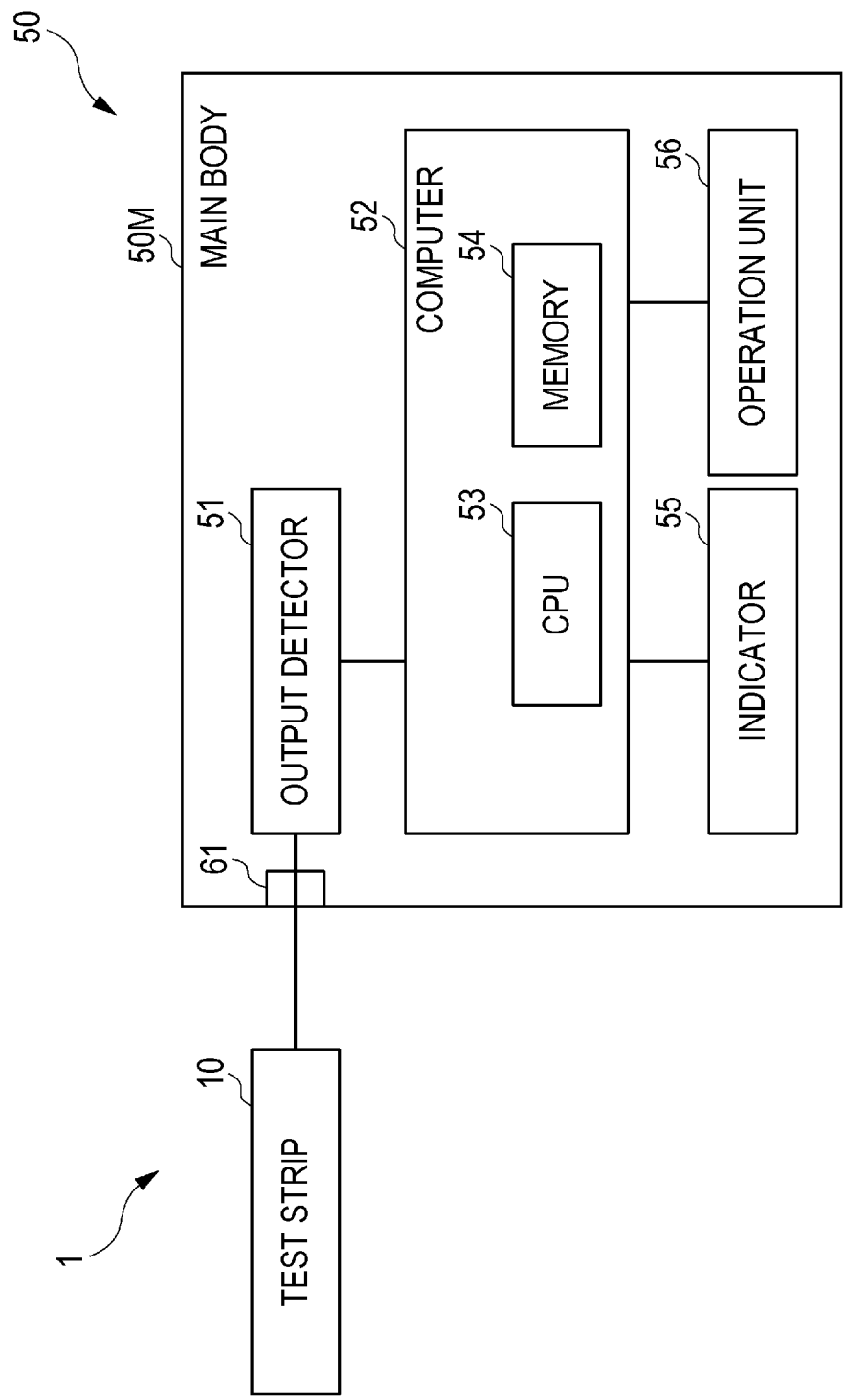

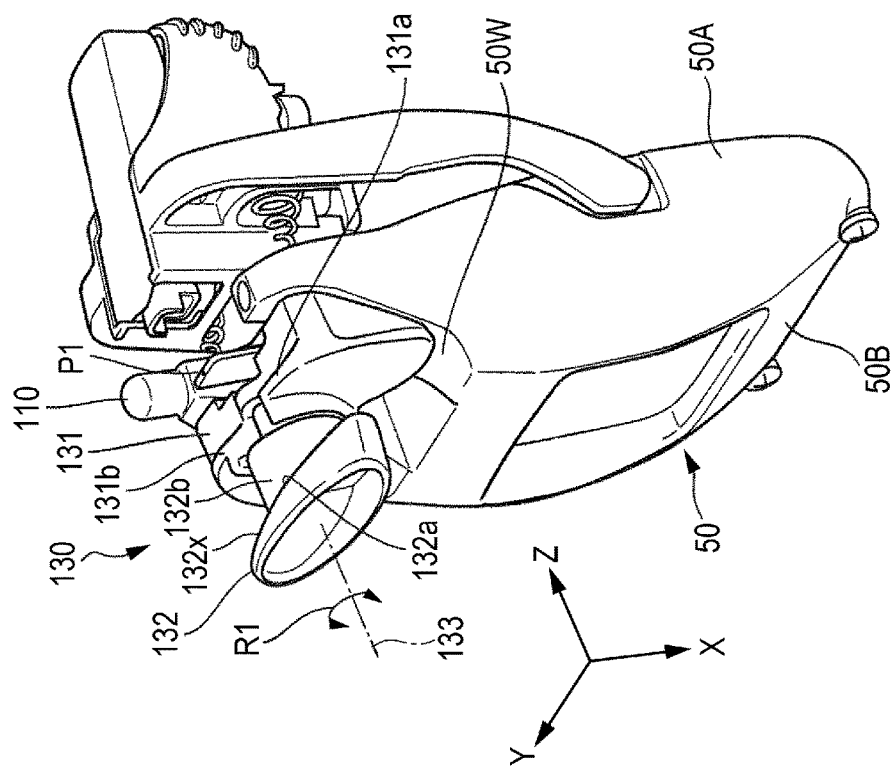
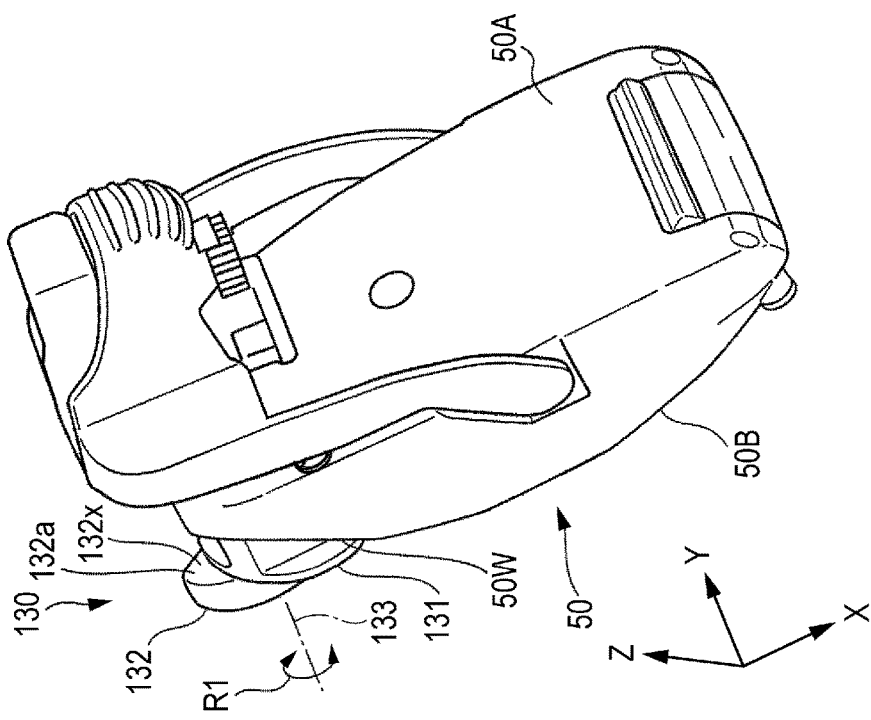
FIG. 17A
FIG. 17B

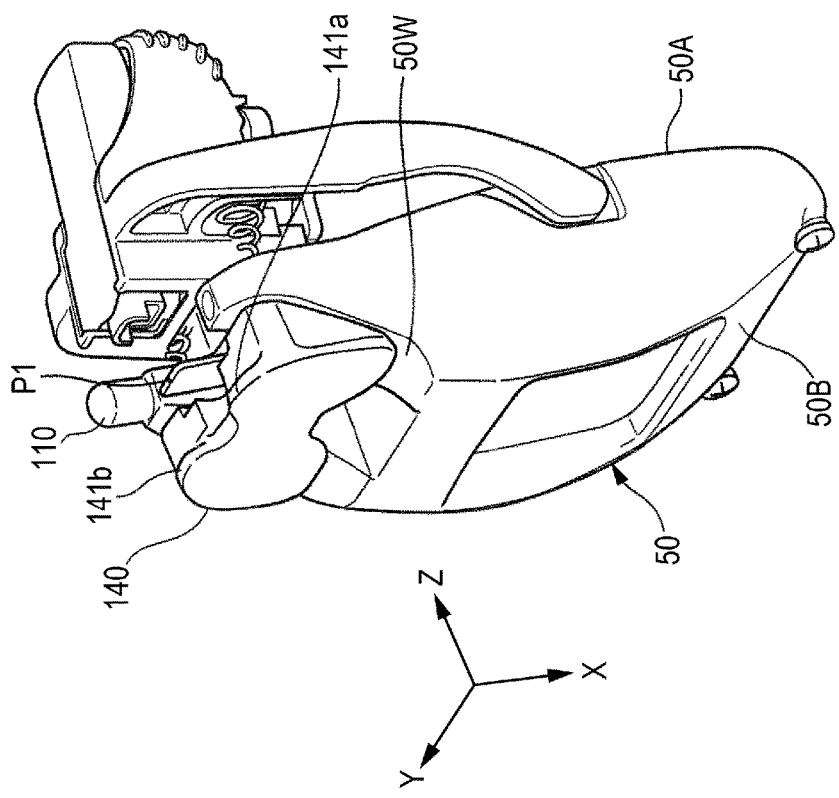
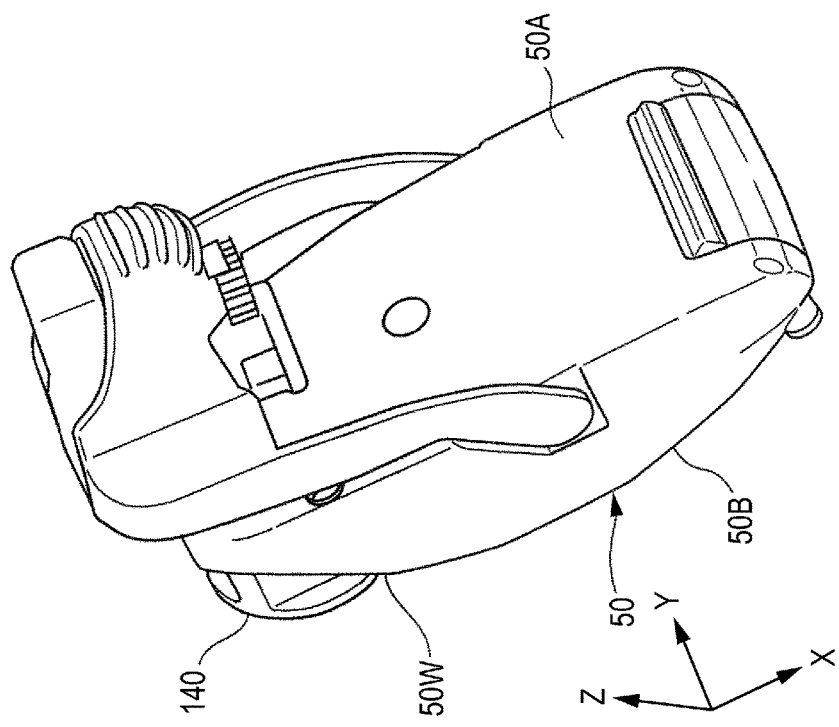

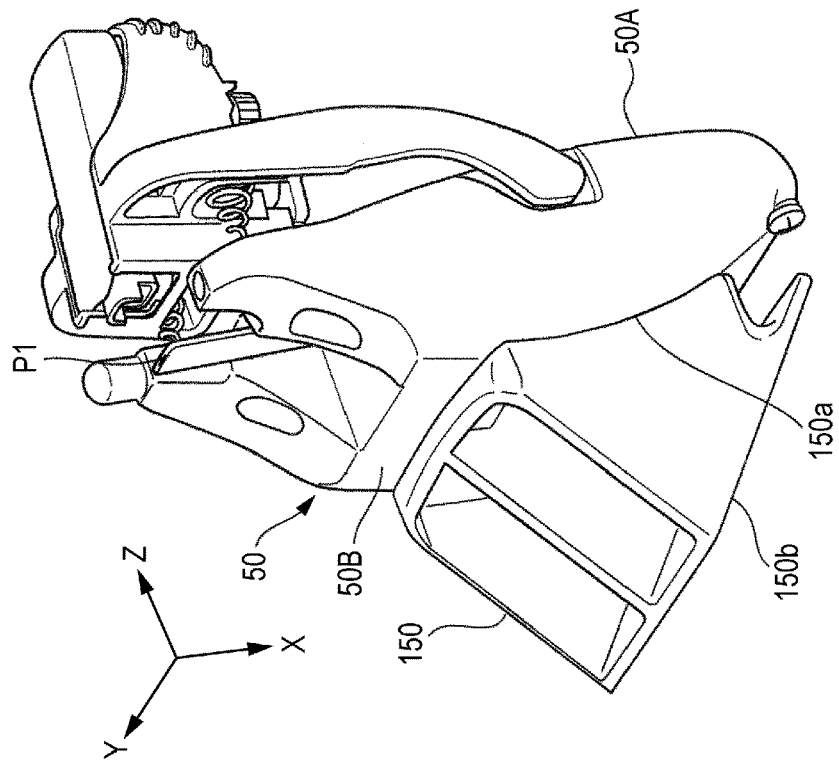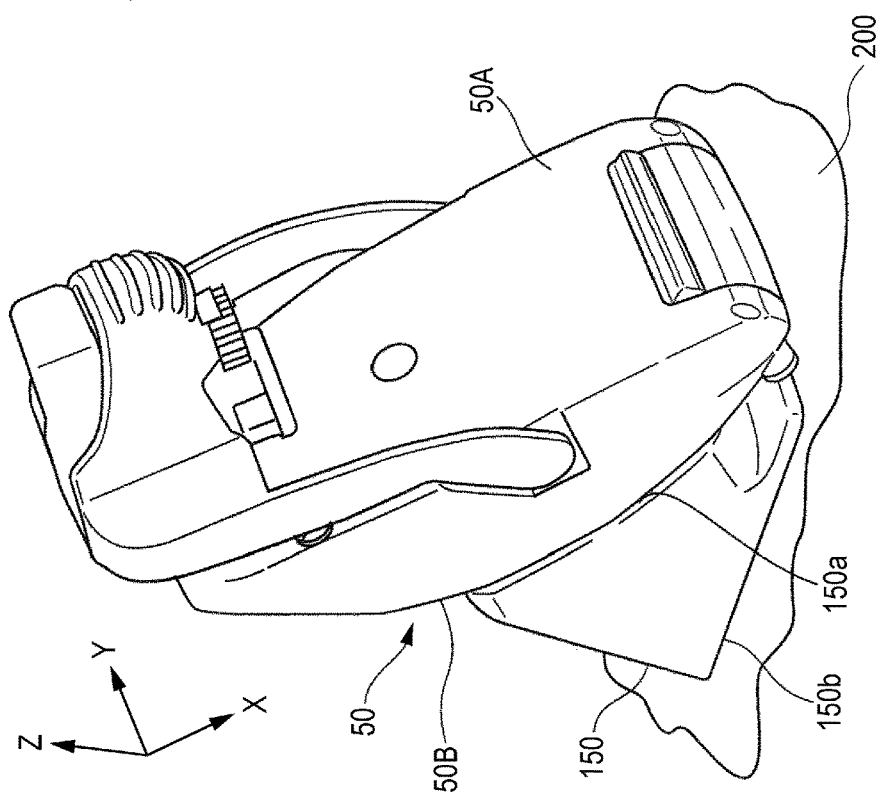

BODILY FLUID-COMPONENT ANALYZING APPARATUS

BACKGROUND OF THE INVENTION

1. Field of the Invention

The present invention relates to a bodily-fluid-component analyzing apparatus, and, in particular, to an integrated bodily-fluid-component analyzing apparatus that obtains a sample of a bodily fluid by pricking a living body with a lancet and measures a component of the sample of the bodily fluid.

2. Description of the Related Art

As a bodily-fluid-component analyzing apparatus of this type, an analyzing apparatus in which a lancet and an analytical sensor are disposed in a housing (called an "integrated analyzing apparatus") is known. For example, Japanese Unexamined Patent Application Publication No. 2005-205096 describes a lancet-sensor integrated device in which a lancet is attached to a housing so as to be movable back and forth and a biosensor is removably attached to the housing. A distal end of the lancet and a sample inlet of the biosensor are located at a distance of 1 mm or less. Thus, when the apparatus is brought into contact with, for example, a finger of a living body, a point (pricked site) on the finger is prick with a lancet, and blood flowing from the pricked site is immediately drawn into the biosensor through the sample inlet.

However, if a subject has hypotension or is old or if the measurement environment is cold, even when a pricked site is pricked with a lancet, blood may not easily flow from the pricked site. In such a case, with existing integrated analyzing apparatuses, it is necessary to perform an operation of temporarily removing the apparatus from a pricked finger and rubbing and squeezing the finger with a hand to cause blood to flow from the pricked site and then applying the blood to the biosensor of the apparatus. Therefore, blood samples may become contaminated, or the component of the blood may be changed due to evaporation of water in the blood. As a result, existing apparatuses have a problem in that the measurement accuracy is low.

SUMMARY OF THE INVENTION

An object of the present invention is to provide an integrated bodily-fluid-component analyzing apparatus that obtains a sample of a bodily fluid by pricking a living body with a lancet and measures a component of the bodily fluid. The apparatus is capable of causing the bodily fluid to flow from a pricked site without fail while the apparatus is placed alongside the living body, and therefore is capable of performing measurement smoothly and accurately.

To achieve the object, the present invention provides an integrated bodily-fluid-component analyzing apparatus, which obtains a sample of a bodily fluid by pricking a living body with a lancet and measures a component of the sample of the bodily fluid, the apparatus including a main body, a lancet holder that is connected to the main body so as to be movable back and forth along a predetermined movement path relative to the main body, a lancet that is removably attached to the lancet holder, and a test strip that is removably attached to the main body and that is used to measure the component of the bodily fluid flowing from a pricked site of the living body pricked with the lancet. The movement path of the lancet holder and a bodily fluid inlet of the test strip face a specific position that is in a vicinity of the main body and at which the pricked site of the living body is to be placed. The apparatus further includes a pressing section that presses a portion of the living body adjacent to the pricked site so as to cause the bodily fluid to flow from the pricked site.

In the present specification, the term "integrated bodily-fluid-component analyzing apparatus" refers to an apparatus that obtains a sample of a bodily fluid by pricking a living body with a lancet and measures a component of the sample of the bodily fluid.

The term "pricked site" refers to a portion of a living body that is to be pricked or that has been pricked (such as a point on a finger).

The term "bodily fluid" typically refers to blood, but may also refer to a bodily fluid other than blood.

With the bodily-fluid-component analyzing apparatus according to the present invention, in a state in which a pricked site of a living body is placed at the specific position in the vicinity of the main body, the lancet holder is moved together with the lancet toward the specific position along a predetermined movement path relative to the main body. Thus, the pricked site of the living body is pricked with the lancet. Because the bodily fluid inlet of the test strip faces the specific position, the bodily fluid flowing from the pricked site is drawn into the test strip through the bodily fluid inlet of the test strip. Thus, a component of the bodily fluid is measured. However, in some cases, it may be difficult for a user to cause the bodily fluid to flow from the pricked site by only pricking the pricked site with the lancet. (In the present specification, the term "user" typically refers to a subject, but may refer to a doctor, a nurse, or another medical worker who takes care of the subject.) In such a case, the user can press a portion of the living body adjacent to the pricked site so as to cause the bodily fluid to flow from the pricked site by using the pressing section without removing the pricked site from the specific position in the vicinity of the main body (that is, while leaving the apparatus to be placed alongside the pricked site of the living body). Therefore, it is possible for the user to cause the bodily fluid to flow from the pricked site without fail. As describe above, the bodily fluid that has flowed from the pricked site is applied to (a sensor portion) of the test strip through the bodily fluid inlet of the test strip. Accordingly, measurement can be smoothly and accurately performed.

After measurement has been finished, the lancet can be removed from the lancet holder and discarded; and the test strip can be removed from the main body and discarded.

Preferably, the main body includes a measurement circuit for measuring the component of bodily fluid by using the test strip and an indicator that indicates a status of measurement of or a result of measurement of the component of the bodily fluid obtained by the measurement circuit. In this case, a user can check the status or the result of measurement of the component of bodily fluid by seeing the indication provided by the indicator.

In one embodiment, the pressing section may be an end surface of the lancet holder facing the specific position.

In this case, a user can repeatedly press a portion of the living body adjacent to the pricked site by moving the lancet holder back and forth along the movement path toward the specific position. Moreover, in this case, the pressing section can be realized simply and at low cost without using an additional member.

In one embodiment, the apparatus may further include an elastic member that urges the lancet holder in a direction away from the specific position relative to the main body.

In this case, when a user stops applying a force to the lancet holder (or reduces the force), the lancet holder returns to a position (initial position) separated from the specific position, and the pricked site of the living body and the vicinity of the pricked site are released. Accordingly, the lancet holder does not obstruct the flow of the bodily fluid from the pricked site.

In one embodiment, the end surface of the lancet holder facing the specific position is frame-shaped so as to surround the lancet.

In this case, when the lancet holder presses a portion of the living body adjacent to the pricked site, the lancet holder can push the bodily fluid from a region around the pricked site toward the pricked site. Thus, it is possible to cause the bodily fluid to flow from the pricked site further without fail.

In one embodiment, the apparatus may further include a mechanism that keeps the lancet retracted in a direction away from the specific position relative to the main body after the lancet has pricked the pricked site of the living body.

In this case, when a user presses a portion of the living body adjacent to the pricked site with the end surface of the lancet holder so as to cause the bodily fluid to flow from the pricked site, the user can repeat pressing without repeating pricking. Thus, it is possible to cause the bodily fluid to flow from the pricked site without fail and without giving an unnecessary pain to a subject.

In one embodiment, the apparatus may further include a positioning element for positioning the pricked site of the living body at the specific position. The positioning element is disposed so as to correspond to a portion of the living body that is outside a blood flow path between a heart and the pricked site of the living body.

In this case, because the positioning element positions the pricked site at the specific position, a user can perform pricking while positioning the pricked site, which is to be pricked, at the specific position without fail. Moreover, because the positioning element does not come into contact with a blood flow path between the heart and the pricked site of the living body, the positioning element does not obstruct the flow for the bodily fluid from the pricked site.

In one embodiment, the positioning element may be attachable to and removable from the main body.

In this case, the positioning element can be attached to the main body in accordance with the position of the pricked site of the living body, which is to be pricked, so that the positioning element may not come into contact with the blood flow path between the heart of the living body and the pricked site.

In one embodiment, the positioning element may include a protrusion that comes into contact with a portion of the living body located on a distal side of the pricked site.

In this case, because the protrusion presses a portion of the living body located on the distal side (farther from the heart) of the pricked site, the protrusion can assist the flow of the bodily fluid from the pricked site.

In one embodiment, the main body may be sized so as to allow a subject, as the living body, to grip the main body with one hand, and the lancet holder may be disposed so as to be moved by a thumb of the one hand along the predetermined path relative to the main body.

In this case, the subject can prick the pricked site and obtain a sample of the bodily fluid by gripping the main body with one hand and moving the lancet holder along the movement path relative to the main body with the thumb of the one hand. That is, the subject can obtain a sample of the bodily fluid with one hand. Moreover, the subject can easily obtain a sample of the bodily fluid, because a thumb can usually generate a stronger force than other fingers. Furthermore, if it is still difficult for the subject to cause the bodily fluid to flow from the pricked site even by repeatedly pressing the pressing section against the portion adjacent to the pricked site, the subject can temporarily remove the pricked site from the specific position in the vicinity of the main body and rub a portion of the living body around the pricked site with his/her hand to cause the bodily fluid to flow from the pricked site. Then, the subject can apply the bodily fluid to the bodily fluid inlet of the test strip. (In this case, however, the sample of bodily fluid may become contaminated, or the component of the bodily fluid may be changed due to evaporation of water in the bodily fluid.)

In one embodiment, when the subject grips the main body with one hand and the thumb of the one hand is in contact with the lancet holder, a specific finger of the one hand other than the thumb may be placed at the specific position in the vicinity of the main body.

In this case, in a state in which the subject grips the main body with one hand and the thumb of the one hand is in contact with the lancet holder, the subject can obtain a sample of the bodily fluid from the pricked site of the specific finger. That is, the subject can obtain a sample of the bodily fluid only with one hand.

In one embodiment, the main body may include a measurement circuit for measuring the component of the bodily fluid by using the test strip. An indicator, which indicates a status or a result of measurement of the component of the bodily fluid performed by the measurement circuit, may be disposed on a part of an outer surface of the main body toward which the lancet holder is to be pressed by the thumb.

In this case, a user can check the status or the result of measuring the component of bodily fluid by seeing the indication provided by the indicator. In particular, because the indicator is disposed on a part of the outer surface of the main body toward which the lancet holder is pressed with the thumb, a subject, as a user, can easily see the indication provided by the indicator while gripping the main body with one hand.

In one embodiment, the apparatus may further include a bottom element that allows the main body to be placed on a flat surface and that is removably attached to or integrated with the main body. When the main body is placed on the flat surface via the bottom element, the specific position, which is in the vicinity of the main body and at which the pricked site of the living body is to be placed, is substantially at the same height from the flat surface as a specific finger of a hand that is placed on the flat surface.

In this case, a subject can place the specific finger (the pricked site) of the hand at the specific position by placing the hand on the flat surface and extending the hand along the main body. Therefore, both the main body and the hand are stably supported by the flat surface. Accordingly, the subject can easily perform the operation of obtaining a sample of the bodily fluid.

As is clear from the above descriptions, with the bodily-fluid-component analyzing apparatus according to the present invention, it is possible to cause the bodily fluid to flow from a pricked site without fail while the apparatus is placed alongside the living body and therefore it is possible to smoothly and accurately perform measurement.

BRIEF DESCRIPTION OF THE DRAWINGS

FIG. 4 is a block diagram of a measurement circuit included in a main body of the bodily-fluid-component analyzing apparatus.

FIGS. 17A and 17B illustrate an example in which another positioning mechanism is disposed in a recess in the back portion of the main body.

FIGS. 18A and 18B illustrate an example in which a positioning member is disposed in the recess in the back portion of the main body.

FIGS. 19A and 19B illustrate an example in which a bottom element, which is used to place the main body on a flat surface, is attached to the main body.

DESCRIPTION OF THE PREFERRED EMBODIMENTS

Hereinafter, embodiments of the present invention will be described in detail with reference to the drawings.

Overall Structure

Figure 1:
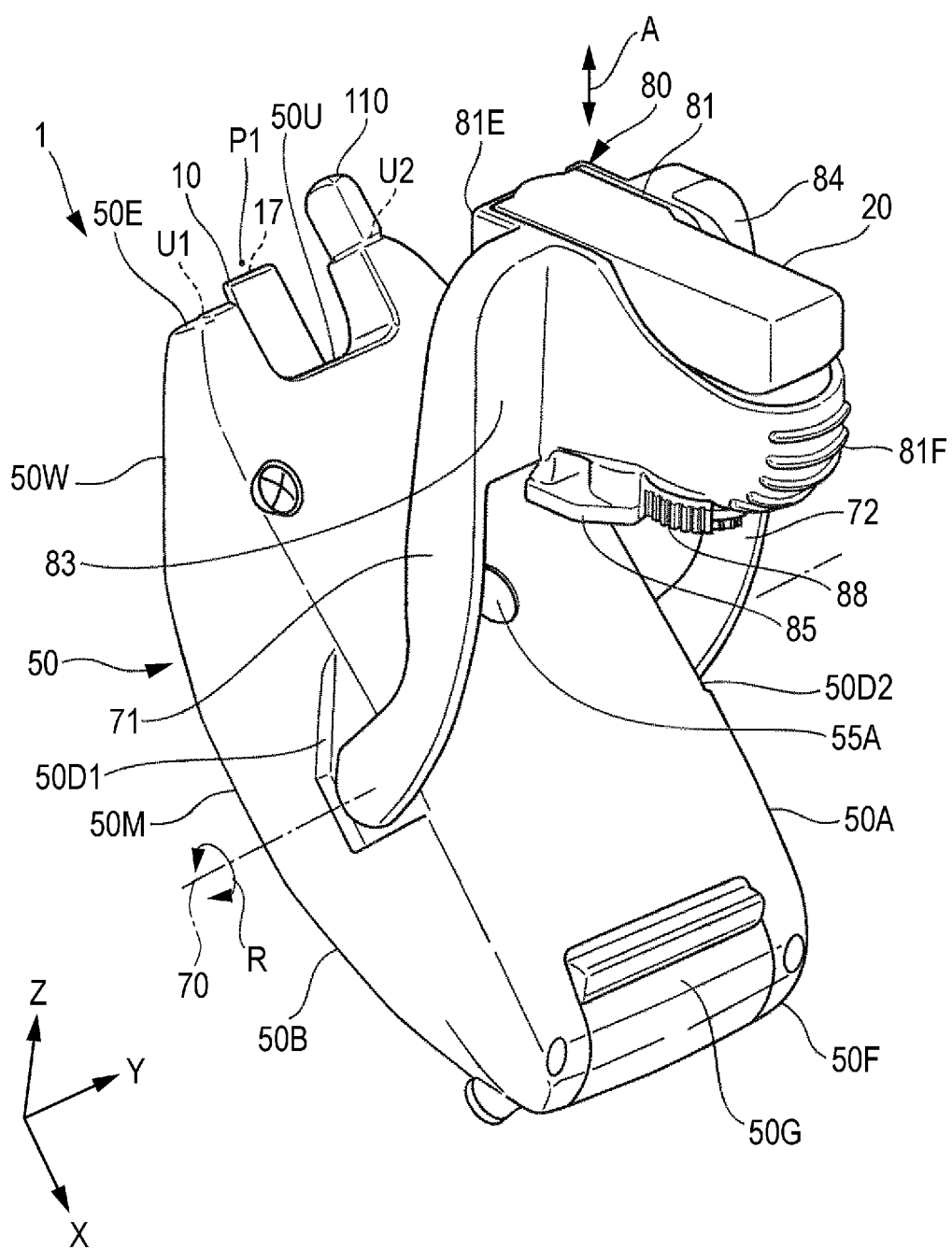
FIG. 1 is a front perspective view of a bodily-fluid-component analyzing apparatus according to an embodiment of the present invention.
Figure 2:
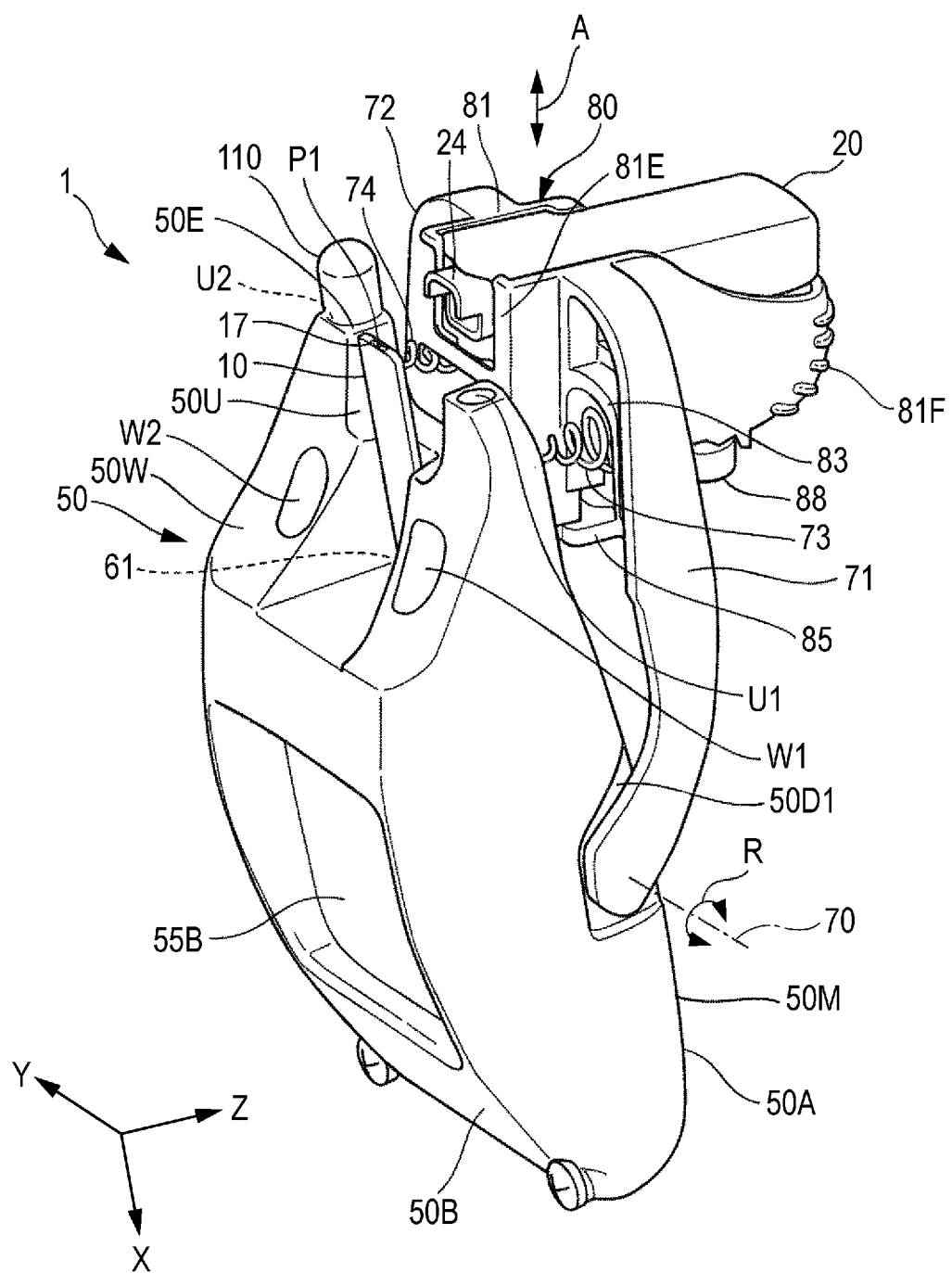
FIG. 2 is a rear perspective view of a bodily-fluid-component analyzing apparatus according to the embodiment of the present invention.

FIG. 1 and FIG. 2 are respectively a front perspective view and a rear perspective view of a bodily-fluid-component analyzing apparatus 1 according to an embodiment of the present invention. The bodily-fluid-component analyzing apparatus 1 includes a main body 50, a lancet holder 80, a test strip 10, and a lancet device 20. The main body 50 accommodates a measurement circuit that measures a component of a bodily fluid. The lancet holder 80 is connected to the main body 50 through a pair of arms 71 and 72. A bodily fluid of a subject, as a living body, is applied to the test strip 10 to measure the concentration of a specific component in the bodily fluid. The lancet device 20 includes a lancet 21 (see, for example, FIG. 10A). The test strip 10 is removably attached to a connector 61 (see FIG. 2) of the main body 50, and the lancet device 20 is removably attached to a container 81 of the lancet holder 80. The bodily-fluid-component analyzing apparatus 1 is an integrated analyzing apparatus that obtains a sample of a bodily fluid by pricking a living body with the lancet 21 and measures a component of the bodily fluid. Examples of a specific component in the bodily fluid include blood glucose, cholesterol, and lactic acid. For ease of understanding, an XYZ-orthogonal coordinate system is shown in each of FIGS. 1 and 2 (and FIGS. 9 and 16A to 19B). The terms "front", "back", "lower/down", and "upper/up", which are used for convenience of description, do not limit the direction in which the main body 50 is disposed.

A casing 50M of the main body 50 includes a front portion 50A, which extends along the XY-plane and is substantially flat; and a back portion 50B, which is convexly curved downward. A light-emitting diode (LED) 55A is disposed in the front portion 50A. A liquid crystal display (LCD) 55B (see FIG. 2) is disposed in the back portion 50B.

A U-shaped recess 50U is formed in an upper end portion 50E (an end portion in the −X direction) of the casing 50M in FIG. 1. The recess 50U allows an end surface 81E of the lancet holder 80 to pass therethrough substantially in the Z direction when pricking is performed as described below. In a state in which the test strip 10 is attached to the connector 61, a bodily fluid inlet 17 of the test strip 10 is located on the back side of the recess 50U. In this example, a position that is in the vicinity of the main body 50 and that faces the bodily fluid inlet 17 of the test strip 10 (to be specific, a position at a distance of 1 mm from the bodily fluid inlet 17 in the −X direction) is a specific position P1 at which a pricked site of the living body is to be placed. Holes U1 and U2 are formed in a pair of end surfaces, on both sides of the recess 50U, of the upper end portion 50E of the casing 50M. A round-bar-shaped protrusion 110, which is an example of a positioning element, can be removably attached to either of the holes U1 and U2. A mark "L", which represents that the hole U2 is to be used to position a finger of a left hand, is attached to a part of the front portion 50A in the vicinity of the hole U2. A mark "R", which represents that the hole U1 is to be used to position a finger of a right hand, is attached to a part of the front portion 50A in the vicinity of the hole U1, which is on the −Y side. In the example shown in FIGS. 1 and 2, the protrusion 110 is attached to the hole U2 on the +Y side, assuming that a finger of a left hand is to be pricked. The marks "L" and "R" are used to locate the protrusion 110 so as to correspond to a portion of a subject that is outside a blood flow path between the heart and the pricked site (as described below in detail). A power supply unit 50G, which accommodates a battery as a power source, is disposed in a lower end portion 50F (an end portion on the +X side) of the casing 50M in FIG. 1.

As illustrated in FIG. 2, a recess 50W is formed near an upper end of the back portion 50B of the casing 50M so as to extend in the Y direction. The recess 50W allows a pricked site of the living body to be placed close to the bodily fluid inlet 17 of the test strip 10 in a state in which the test strip 10 is attached to the connector 61. Holes W1 and W2, into which an additional positioning element can be fitted as described below, are formed in the recess 50W.

The main body 50 is sized so as to allow a subject, as a living body, to grip the main body 50 with one hand. For example, the dimensions of the main body 50 in the X, Y, and Z directions are respectively in the ranges of about 8 cm to 10 cm, about 4 cm to 5 cm, and about 2.5 cm to 5 cm.

As illustrated in FIGS. 1 and 2, the pair of arms 71 and 72 are attached to the main body 50 so that the arms 71 and 72 can rotate, as indicated by an arrow R, around an axis 70 that extends through substantially the center of the main body 50 in the Y direction. A pair of recesses 50D1 and 50D2, which are formed in side portions of the main body 50, restrict the movable range of the arms 71 and 72 to, approximately, a range from an angular position shown in FIG. 1 to an angular position at which the end surface 81E of the lancet holder 80 reaches the specific position P1. The lancet holder 80, which holds the lancet device 20, is integrally formed with distal end portions (end portions farther from the axis 70) of the pair of arms 71 and 72 via connection plates 83 and 84. The lancet holder 80 is connected, through the arms 71 and 72, to the main body 50 so as to be movable back and forth along a predetermined movement path relative to the main body 50 (to be specific, along a path that is centered around the axis 70 and that has a radius substantially the same as the length of the arms 71 and 72). The length of the arms 71 and 72 is in the range of about 4 cm to 6 cm.

The lancet device 20 (the structure and operation of which will be described below) is a commercially marketed lancet device having an oblong substantially rectangular shape.

The lancet holder 80 includes the container 81 for containing the lancet device 20. The container 81 extends in a direction substantially perpendicular to the arms 71 and 72. The container 81 has an angular-U-shaped cross section (see FIG. 2) that opens upward and that surrounds the lancet 21. The end surface 81E of the container 81 facing the specific position P1 serves as a pressing section that presses portions 92, 93, and 96 (see FIG. 9) of the living body, which are adjacent to the pricked site. With this structure, the pressing section can be realized simply and at low cost without using an additional member. As illustrated in FIGS. 1 and 2, a plurality of protrusions and recesses are formed on an end surface 81F of the container 81 facing away from the specific position P1. The protrusions and recesses serve to prevent slipping when a subject presses the lancet device 20, including the lancet holder 80, toward a pricked site (the specific position P1).

A position adjustment member 85 and a position adjustment screw 88 are disposed below the container 81 in FIGS. 1 and 2. The position adjustment screw 88 is used to slide the position adjustment member 85 relative to the container 81 in a direction (indicated by an arrow A) in which the arms 71 and 72 extend. The position of the lancet device 20 (that is, the lancet 21) in the direction indicated by the arrow A can be adjusted by moving the position adjustment member 85 by rotating the position adjustment screw 88. Thus, when performing pricking, the position of the lancet device 20 can be adjusted in the X direction so that the lancet 21 accurately points toward the pricked site (the specific position P1). (Note that displacement of the lancet device 20 in the Y direction does not cause a serious problem.)

As illustrated in FIG. 2, conical coil springs 73 and 74, which are examples of an elastic member, are respectively attached to the back sides of the connection plates 83 and 84. The conical coil springs 73 and 74 come into contact with the front portion 50A of the main body 50 and urge the lancet holder 80 in a direction away from the specific position P1 relative to the main body 50.

The elastic member is not limited to the conical coil springs 73 and 74 and may be any member that can urge the lancet holder 80 relative to the main body 50 in a direction away from the specific position P1 relative to the main body 50. Preferably, the elastic member is attached to at least one of the lancet holder 80 and the main body 50.

Structure of Test Strip

Figure 3A:
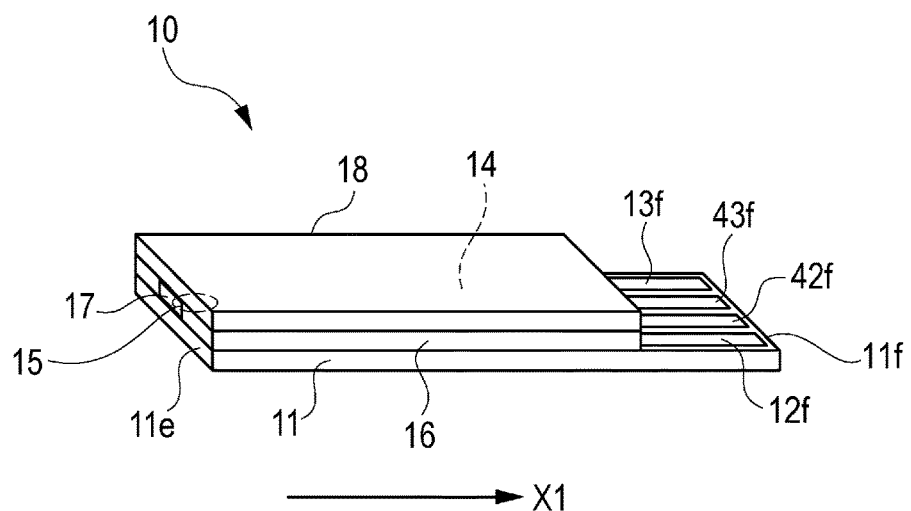
FIG. 3A illustrates the structure of a test strip used for the bodily-fluid-component analyzing apparatus.

As illustrated in FIG. 3A, the test strip 10 includes a substrate 11, a spacer 16, and a cover sheet 18.

In this example, the substrate 11 is made of an insulating plastic material and has a rectangular shape that is elongated in one direction (in the X1 direction in FIG. 3A).

On an upper surface of the substrate 11 in FIG. 3A, a pair of a working electrode 12 and a reference electrode 13 are disposed so as to be separated from each other. Each of the working electrode 12 and the reference electrode 13 extends in a strip-like shape in the X1 direction from a first end 11e to a second end 11f of the substrate 11. A first pair of electrode terminals 12f and 13f, which are end portions of the working electrode 12 and the reference electrode 13, are exposed in a region near the second end 11f of the substrate 11 (on the +X1 side). Parts of the working electrode 12 and the reference electrode 13 other than the first pair of electrode terminals 12f and 13f are covered by the spacer 16 and the cover sheet 18.

On the upper surface of the substrate 11, a pair of conductors 42 and 43 are disposed between the working electrode 12 and the reference electrode 13 so as to be separated from each other. Each of the conductors 42 and 43, which are connected to a resistor portion 14 (described below), extends in a strip-like shape in the X1 direction. A second pair of electrode terminals 42f and 43f, which are end portions of the conductors 42 and 43, are exposed in a region near the second end 11f of the substrate 11 (on the +X1 side). Parts of the conductors 42 and 43 other than the second pair of electrode terminals 42f and 43f are covered by the spacer 16 and the cover sheet 18.

In a region near the first end 11e of the substrate 11 (on the −X1 side), a sensor portion 15, which includes a reagent layer, is disposed so as to extend between the working electrode 12 and the reference electrode 13. In this example, in order to measure the blood glucose level, the sensor portion 15 includes an iron complex or a Ru complex in which glucose dehydrogenase or glucose oxidase is dispersed. A part of the spacer 16 directly above the sensor portion 15 is cut out. Thus, the sensor portion 15 faces the cover sheet 18 at a distance equal to the thickness of the spacer 16. When blood comes into contact with the bodily fluid inlet 17, which is formed by cutting out the spacer 16, the bodily fluid is drawn into a gap between the sensor portion 15 and the spacer 16 due to capillary action and applied to the sensor portion 15.

Figure 3B:
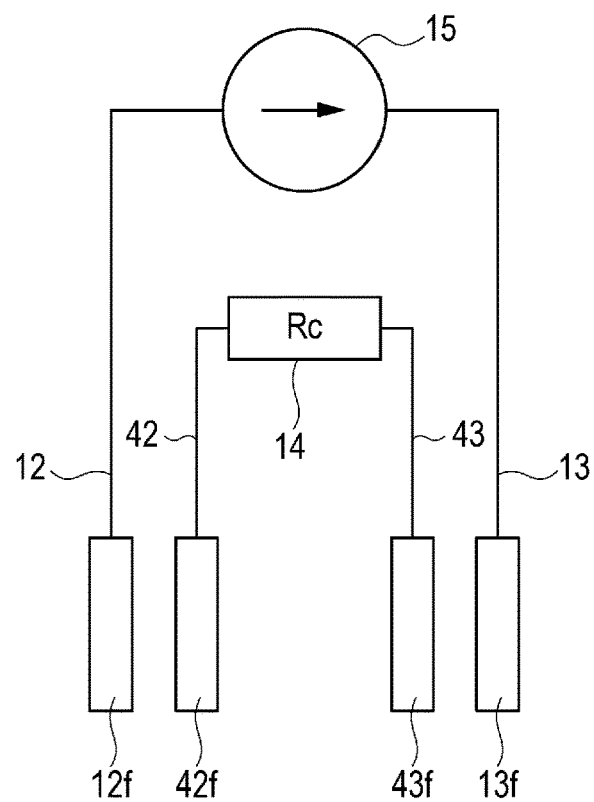
FIG. 3B illustrates an equivalent circuit of the test strip.

The resistor portion 14 is disposed at substantially the center of the substrate 11. Referring to FIG. 3B, which shows an equivalent circuit of the test strip 10, the resistor portion 14 has an electric resistance Rc that represents attribute information, including the sensitivity, of the test strip 10. The term "attribute information" refers to, for example, information representing the sensitivity of the test strip 10 or information used to select a calibration curve that is suitable for a component to be measured.

In a state (referred to as "bodily-fluid-unapplied state") in which a bodily fluid (blood) of a subject is not applied to the sensor portion 15 of the test strip 10, the electric resistance of the sensor portion 15 can be practically regarded as infinite.

In a state (referred to as "bodily-fluid-applied state") in which the bodily fluid of the subject is attached to the test strip 10 and in contact with the sensor portion 15, the sensor portion 15 generates an electric current as illustrated in FIG. 3B.

Measurement Circuit of Main Body

As shown in the block diagram of FIG. 4, the casing 50M of the main body 50 accommodates the connector 61, into which the test strip 10 is inserted; an output detector 51, which detects an output of the test strip 10 through the connector 61; and a computer 52.

The computer 52 includes a central processing unit (CPU) 53, as a controller, and a memory 54.

The memory 54 stores data of a program for controlling the bodily-fluid-component analyzing apparatus 1, data of a calibration curve representing the relationship between the blood glucose level and the electric current generated by the sensor portion 15; and data of measurement results. In this example, the memory 54 stores data of a plurality of calibration curves so that the apparatus 1 can deal with variation in the sensitivity of (the sensor portion 15 of) the test strip 10 (that is, variation in the relationship between the blood glucose level and the electric current generated by the sensor portion 15). The memory 54 is also used as a work memory when executing the program.

The CPU 53 controls the bodily-fluid-component analyzing apparatus 1 in accordance with the program stored in the memory 54. Specific control methods will be described below.

An indicator 55 includes the LED 55A and the LCD 55B (described above), which are controlled by the computer 52. In this example, the LED 55A is used to indicate a status of measurement, and the LCD 55B is used to display a result of measuring the concentration of a specific component in a bodily fluid (in this example, the blood glucose level) and other information.

Figure 5:
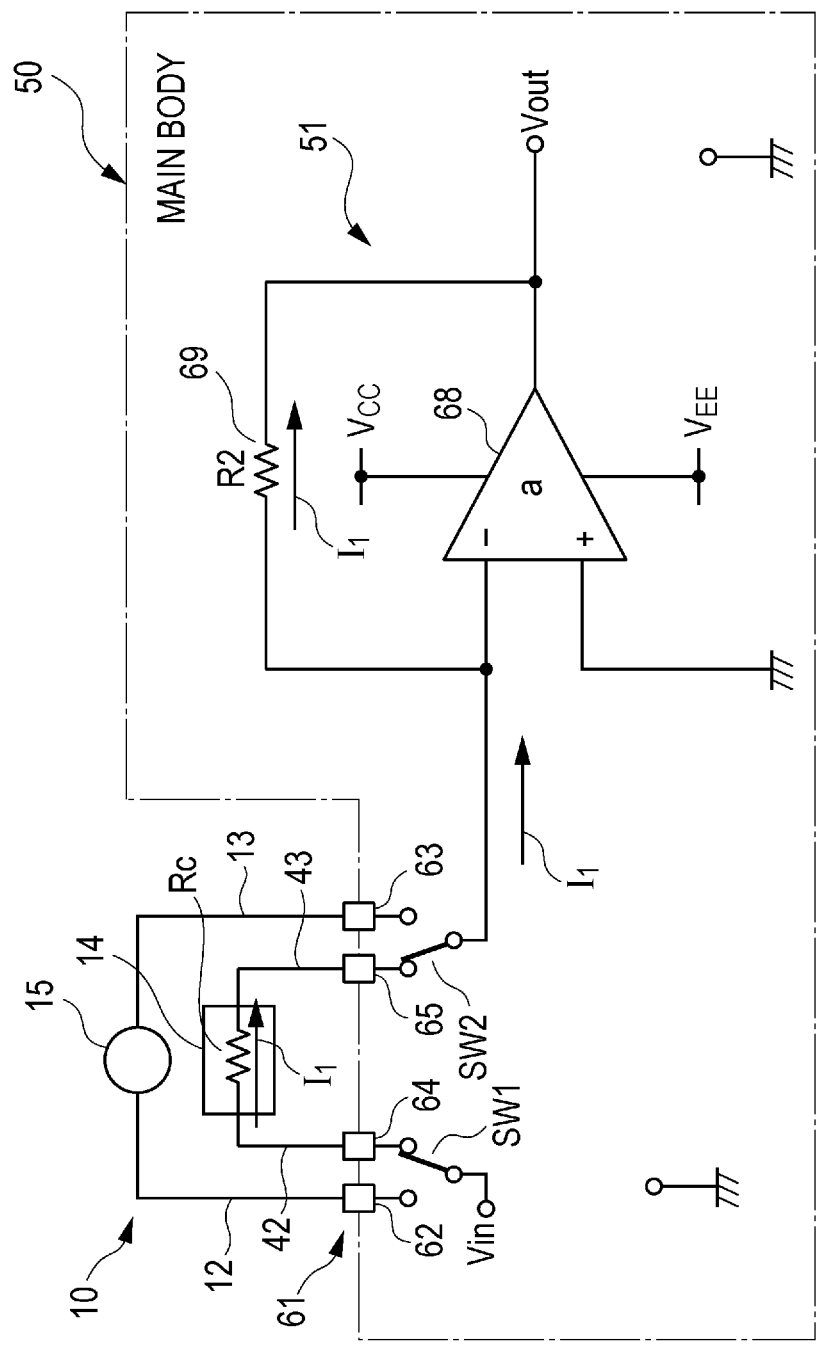
FIG. 5 is a diagram illustrating how the measurement circuit detects attribute information from the test strip in a bodily-fluid-unapplied state.

As illustrated in FIG. 5, specifically, the output detector 51 includes an operation amplifier 68 (hereinafter, referred to as an "op-amp 68"), a feedback resistor 69 (having a resistance R2), a power source (not shown), and switches SW1 and SW2. The op-amp 68 is interconnected between a power source potential $V_{cc}$ and a potential $V_{EE}$, which is lower than the power source potential $V_{cc}$. The feedback resistor 69 is interconnected between the inverting terminal (−) and the output terminal (which outputs an output voltage Vout) of the op-amp 68. The power source (not shown) applies a predetermined voltage Vin to the resistor portion 14 or the sensor portion 15 of the test strip 10. The switches SW1 and SW2 switch between the first pair of contacts 62 and 63 and the second pair of contacts 64 and 65. An output current from the reference electrode 13 of the test strip 10, which is an output of the test strip 10, is input to the inverting terminal (−) of the op-amp 68. The non-inverting terminal (+) of the op-amp 68 is grounded. With this structure, the output detector 51 outputs the output voltage Vout in accordance with the output (output current) of the test strip 10.

Generally, the output voltage of the op-amp 68 can be represented as $$Vout = -(R2/R1) \times Vin \quad (1)$$

where R1 is the electric resistance of the test strip 10.

Operation of Main Body

Figure 7:
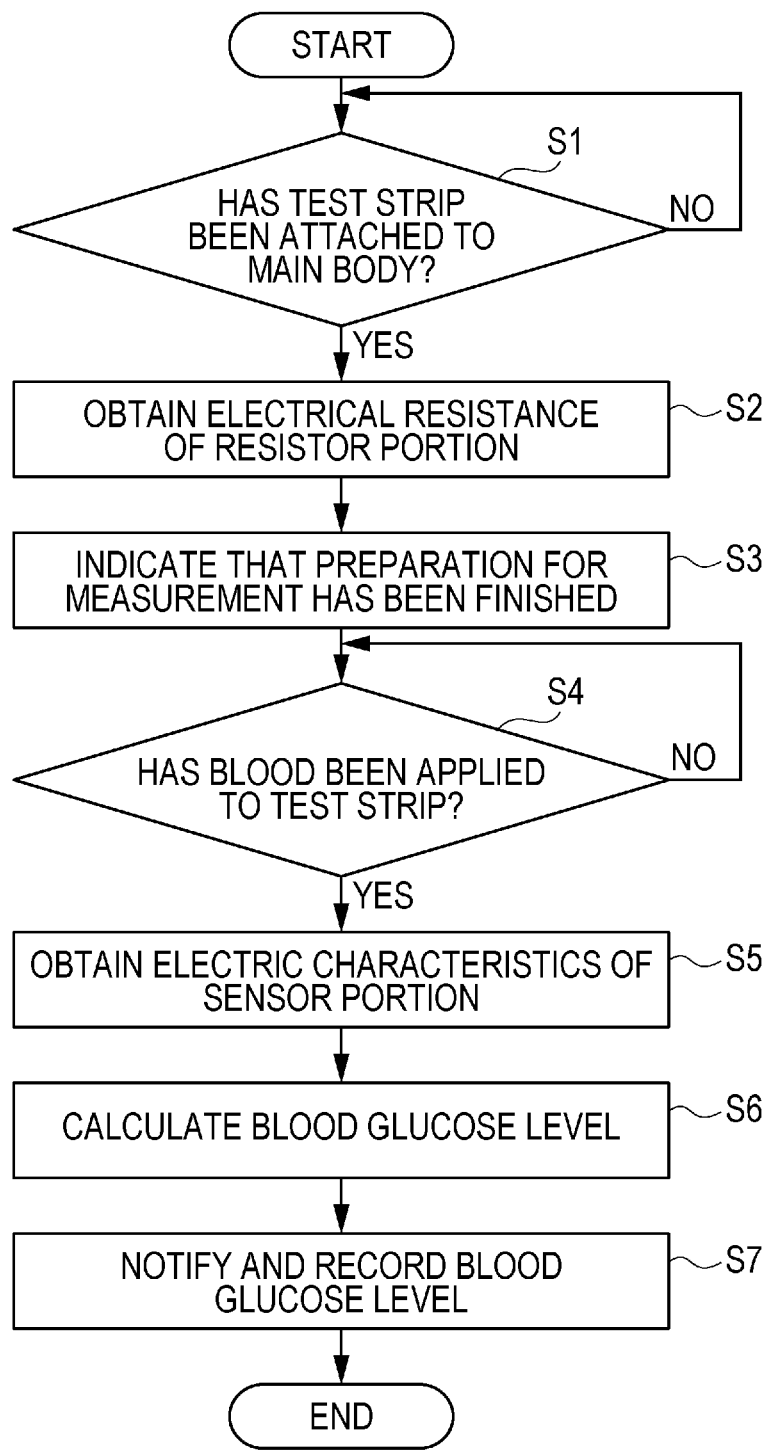
FIG. 7 is a flowchart of a process through which the measurement circuit measures the blood glucose level.

Next, referring the flowchart of FIG. 7, the operation of the main body 50 will be described.

i) First, as shown in step S1 of FIG. 7, the CPU 53 of the main body 50 determines whether or not the test strip 10 has been attached to the connector 61.

In this example, the CPU 53 causes the switches SW1 and SW2 of the output detector 51 to select the second pair of contacts 64 and 65 as illustrated in FIG. 5. In this state, the CPU 53 determines whether or not the test strip 10 has been attached to the connector 61 on the basis of a change in the output voltage Vout of the output detector 51 shown in FIG. 5. That is, if the test strip 10 has not been attached, the output voltage Vout of the output detector 51 is substantially zero. On the other hand, if the test strip 10 in a bodily-fluid-unapplied state has been attached, R1=Rc (finite value) in expression (1), and therefore the output voltage Vout of the output detector 51, which is represented as in the following expression (2), is not substantially zero.

$$Vout = -(R2/Rc) \times Vin \quad (2)$$

On the basis of the change in the output voltage Vout, the CPU 53 determines whether or not the test strip 10 has been attached to the connector 61. (Here, it is assumed that the values of R2 and Vin and the range of the value of Rc are known beforehand).

To be specific, in accordance with expression (2), the range of the value of the output voltage Vout is determined by the values of R2 and Vin and the range of the value of Rc. The lower limit $V_L$ and the upper limit $V_U$ of the range of the value of the output voltage Vout are set beforehand. If the output voltage Vout is between the lower limit $V_L$ and the upper limit $V_U$ at this stage, the CPU 53 determines that the test strip 10 in a bodily-fluid-unapplied state has been attached. If the output voltage Vout is lower than the lower limit $V_L$, the CPU 53 determines that the test strip 10 has not been attached. If the output voltage Vout is higher than the upper limit $V_U$, the CPU 53 determines that a malfunction has occurred (in this case, the CPU 53 causes the indicator 55 to indicate that a malfunction has occurred).

Alternatively or additionally, at this stage, a subject may input, by operating an operation unit 56 (see FIG. 4), that the test strip 10 has been attached. Thus, the CPU 53 can determine without fail that the test strip 10 in a bodily-fluid-unapplied state has been attached.

ii) Next, it is assumed that the test strip 10 has been attached to the main body 50 in a bodily-fluid-unapplied state. Then, the electrode terminals 12f and 13f of the working electrode 12 and the reference electrode 13 and the electrode terminals 42f and 43f of the conductors 42 and 43 (see FIG. 3A), which are disposed on the substrate 11, are respectively in contact with the contacts 62, 63, 64, and 65 of the connector 61 shown in FIG. 5. As shown in step S2 of FIG. 7, in this state, the CPU 53 obtains the electric resistance Rc, which represents the attribute information, from the resistor portion 14 of the test strip 10 through the contacts 64 and 65 and the conductors 42 and 43.

To be specific, as illustrated in FIG. 5, due to application of the voltage Vin, an electric current (denoted by $I_1$) flows through the working electrode 12, the resistor portion 14, the reference electrode 13, and the feedback resistor 69 on the substrate 11. In this state, the CPU 53 detects the output voltage Vout (denoted by Vout1) of the output detector 51. Thus, the CPU 53 can calculate the electric resistance Rc, which represents the attribute information of the test strip 10 (in this example, the sensitivity of the sensor portion 15, that is, a correspondence between the blood glucose level and the electric current generated by the sensor portion 15), by using the following expression (3).

$$Rc = -R2 \times (Vin/Vout1) \qquad (3)$$

Figure 20:
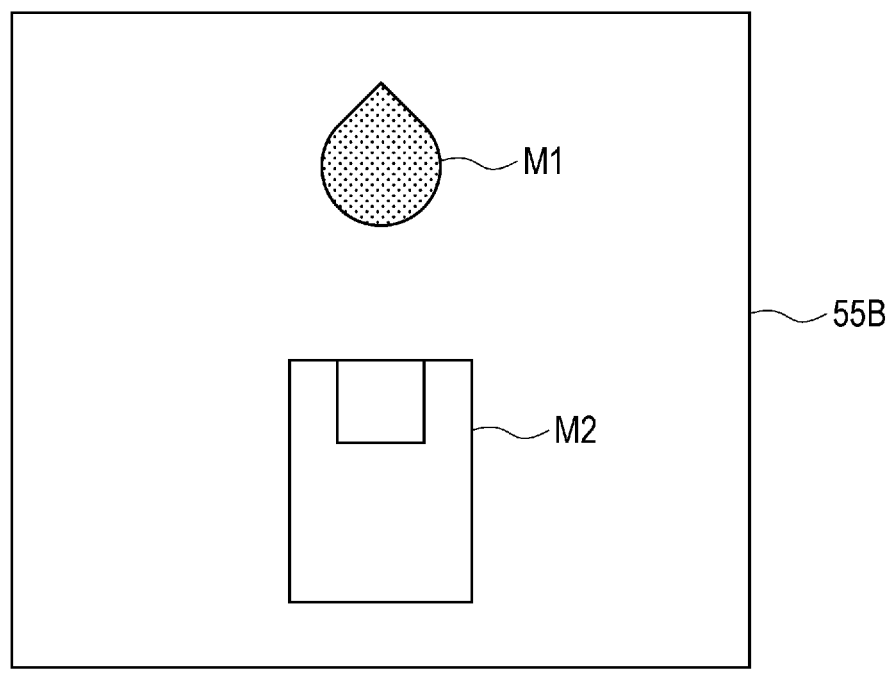
FIG. 20 illustrates an example of an image displayed on the LCD to prompt a subject to apply blood to the test strip.

The correspondence between the blood glucose level and the electric current generated by the sensor portion 15, which is represented by the electric resistance Rc, is stored, as a calibration curve, in the memory 54 (see FIG. 4).

iii) As shown in step S3 of FIG. 7, when the electric resistance Rc of the resistor portion 14 has been obtained, the CPU 53 causes the indicator 55 to indicate that preparation for measurement has been finished and notifies a user. For example, the CPU 53 causes the LCD 55B to display that "Preparation for measurement is finished. Please apply blood to the test strip". Alternatively or additionally, the CPU 53 may turn the LED 55A on and off so as to prompt a subject to apply blood to the test strip 10; or the CPU 53 may cause the LCD 55B to display a mark M1, representing blood, and a mark M2, representing the test strip, as shown in FIG. 20.

iv) Next, as shown in step S4 of FIG. 7, the CPU 53 determines whether or not blood has been applied to the test strip 10.

Figure 6:
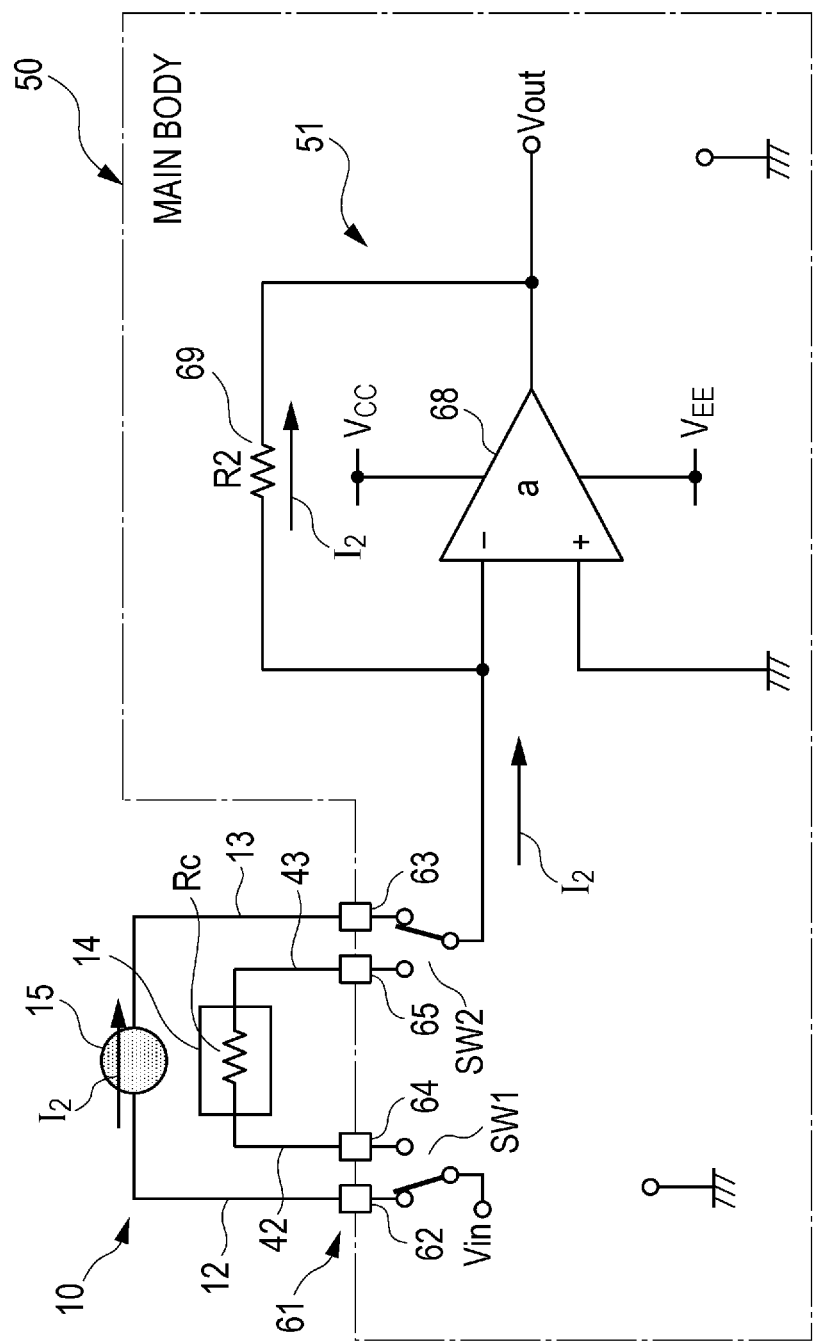
FIG. 6 is a diagram illustrating how the measurement circuit detects the concentration of a specific component in a bodily fluid from the test strip in a bodily-fluid-applied state.

In this example, the CPU 53 causes the switches SW1 and SW2 of the output detector 51 to select the first pair of contacts 62 and 63 as illustrated in FIG. 6. In this state, the CPU 53 determines whether or not blood has been applied to the test strip 10 on the basis of a change in the output voltage Vout of the output detector 51. That is, in a bodily-fluid-unapplied state, the output voltage Vout of the output detector 51 is substantially zero. On the other hand, in a bodily-fluid-applied state, as shown in FIG. 6, the sensor portion 15 causes an electrochemical reaction with blood and generates an electric current (denoted by $I_2$) as a change in electric characteristics. In this case, due to application of the voltage Vin, the electric current $I_2$ flows through the contacts 62 and 63 and the working electrode 12 and the reference electrode 13 on the substrate 11. In the bodily-fluid-applied state, the CPU 53 detects the output voltage Vout (denoted by Vout2) of the output detector 51, which is generated in accordance with the electric current $I_2$. On the basis of the change in the output voltage Vout from zero to Vout2, the CPU 53 determines whether or not blood has been applied to the test strip 10. To be specific, if the output voltage Vout2 is higher than the aforementioned upper limit $V_U$ at this stage, the CPU 53 determines that blood has been applied to the test strip 10.

Alternatively or additionally, at this stage, a subject may input, by operating the operation unit 56 (see FIG. 4), that blood has been applied to the test strip 10. Thus, the CPU 53 can determine without fail that blood has been applied to the test strip 10.

v) In the bodily-fluid-applied state, as shown in step S5 of FIG. 7, the CPU 53 obtains the electric characteristics of the sensor portion 15. To be specific, the CPU 53 detects the electric current $I_2$ as the electric characteristics of the sensor portion 15.

vi) Next, as shown in step S6 of FIG. 7, the CPU 53 calculates the blood glucose level on the basis of the electric current $I_2$ of the sensor portion 15 in the bodily-fluid-applied state and the calibration curve (stored in the memory 54) of the test strip 10, which is represented by the electric resistance Rc of the resistor portion 14.

vii) Subsequently, as shown in step S7 of FIG. 7, the CPU 53 turns on the LED 55A continuously to notify a user that measurement has been finished. Moreover, the CPU 53 causes the LCD 55B to display the calculated blood glucose level as, for example, "Blood Glucose Level 180 mg/dL". Furthermore, the CPU 53 stores the value of the blood glucose level in the memory 54. A user (for example, a subject) can cause the indicator 55 to indicate the blood glucose level stored in the memory 54 by operating the operation unit 56 (see FIG. 4).

Thus, the main body 50 can measure the blood glucose level of a subject accurately, even if the sensitivity of the test strip 10 (in particular, the sensor portion 15) has variation.

Operation Performed by Subject

Figure 8:
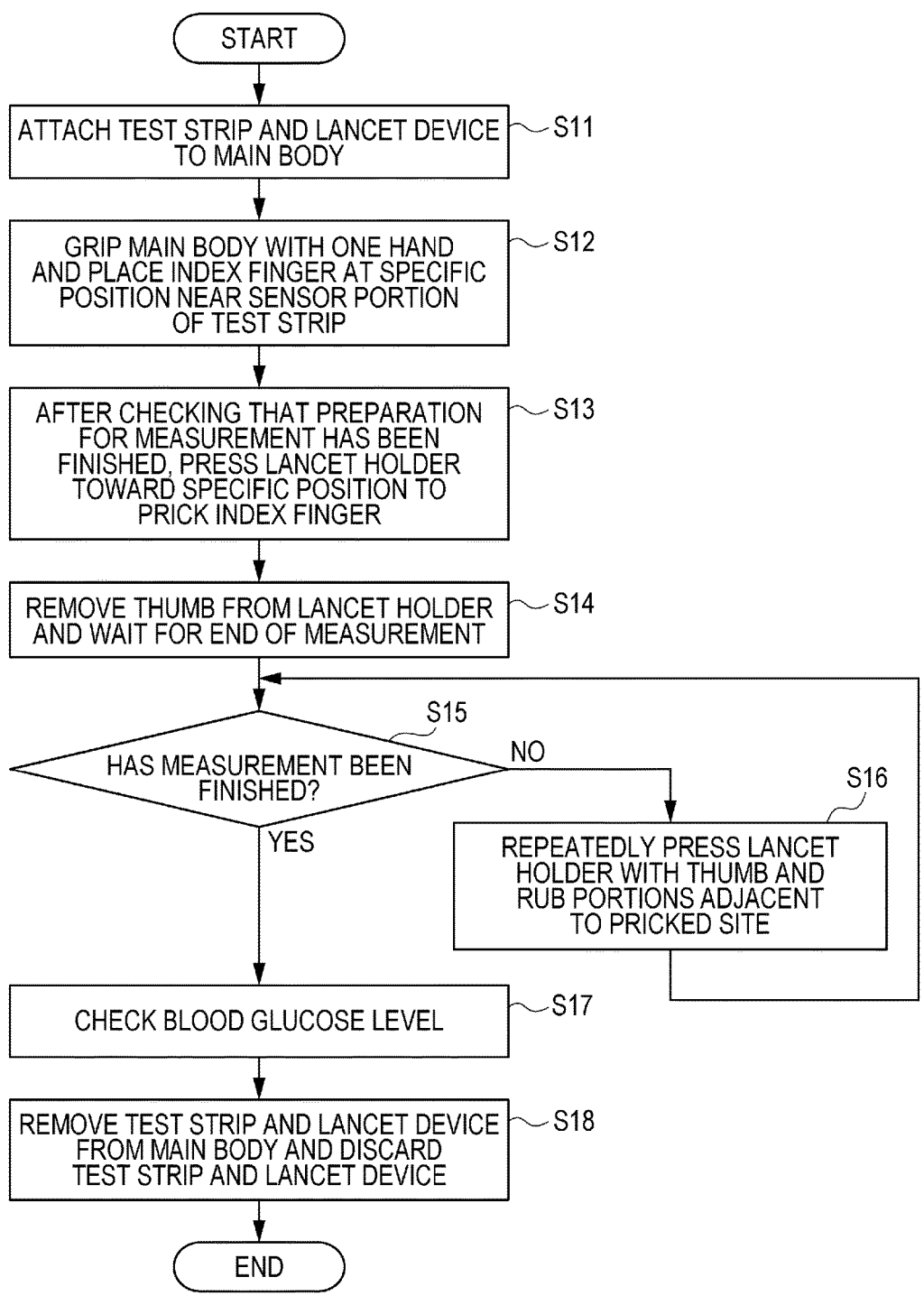
FIG. 8 is a flowchart of an operation performed by a subject to measure the blood glucose level.
Figure 9:
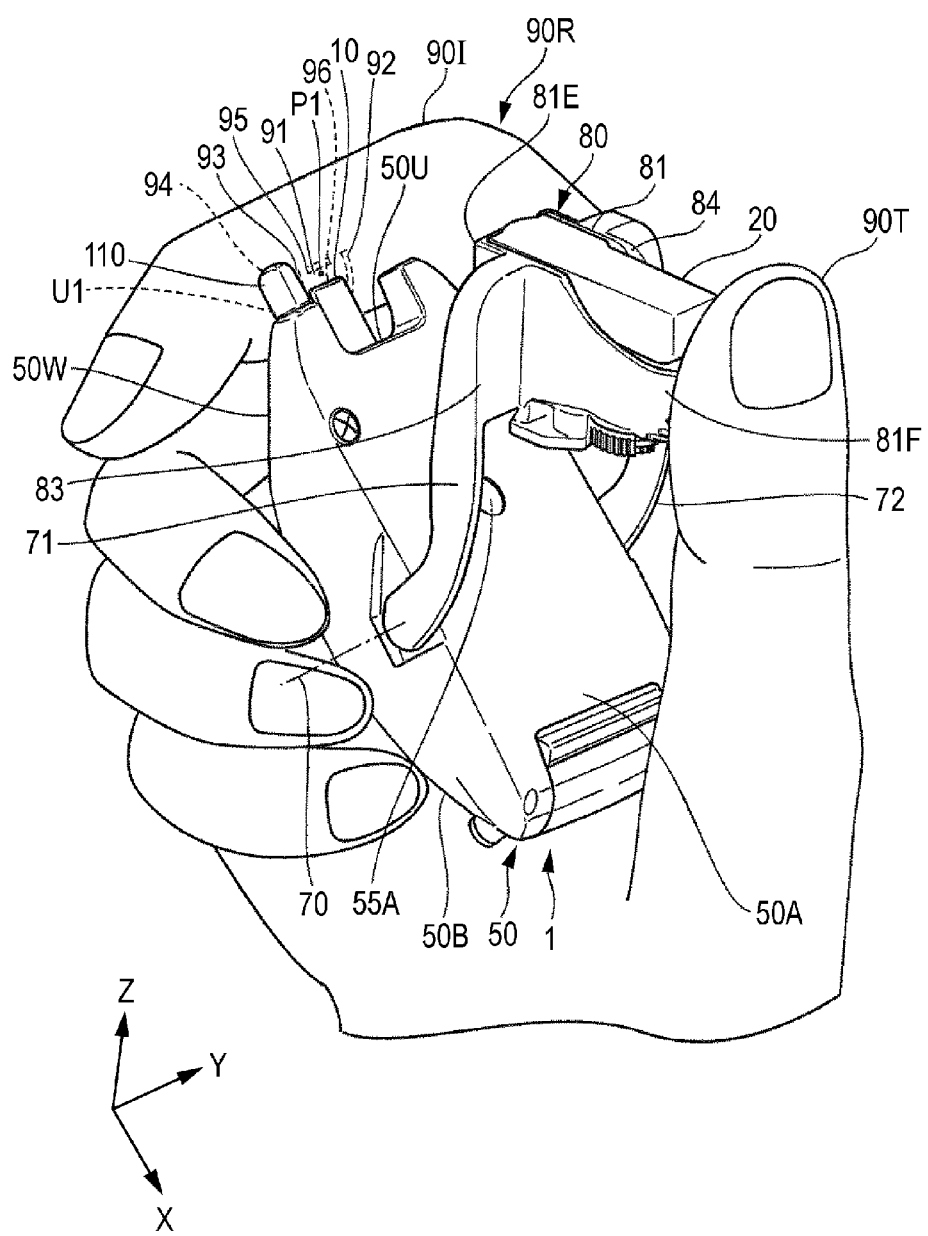
FIG. 9 illustrates the main body of the bodily-fluid-component analyzing apparatus in a state in which a subject grips the main body with one hand (in this example, the right hand).

FIG. 8 is a flowchart of an operation performed by a subject. Next, referring to FIGS. 9 to 14B, the operation performed by the subject to measure the blood glucose level will be described. FIG. 9 illustrates the main body 50 in a state in which the subject grips the main body 50 with one hand (in this example, the right hand 90R). FIGS. 10A, 11A, 12A, 13A, and 14A are longitudinal sectional views (taken along the ZX-plane in FIG. 9) of the main body 50 when the operation progresses from the state shown in FIG. 9. Correspondingly, FIGS. 10B, 11B, 12B, 13B, and 14B illustrate the inside of the lancet device 20 as viewed from above.

As illustrated in FIG. 9, it is assumed, for example, that the subject pricks a side surface of the index finger 90I of the right hand 90R as a pricked site 91. In this case, the subject attaches the protrusion 110, as a positioning element, beforehand to the hole U1 in the main body 50 having the mark "R". That is, the protrusion 110 is placed so as to correspond to a portion of the subject that is outside a blood flow path between the heart and the pricked site 91.

First, as shown in step S11 of FIG. 8, the subject attaches the test strip 10 to the connector 61 of the main body 50 and attaches the lancet device 20 to the container 81 of the lancet holder 80. Next, as illustrated in FIG. 9, the subject grips the main body 50 with one hand (in this example, the right hand 90R) and brings the thumb 90T of the right hand 90R into contact with the end surface 81F of the lancet holder 80 farther from the specific position P1. Moreover, the subject places a side surface of the index finger 90I of the right hand 90R at the specific position P1 near the sensor portion 15 (the bodily fluid inlet 17) of the test strip 10 (step S12 in FIG. 8). A point on the side surface of the index finger 90I corresponding to the specific position P1 is the pricked site.

At this time, the protrusion 110 is in contact with a portion 94 of the subject located on the distal side (a side farther from the heart) of the pricked site 91 of the index finger 90I. Thus, the protrusion 110 serves as a positioning element and restricts displacement of the index finger 90I in the +Z direction. The protrusion 110 does not come into contact with a blood flow path of the subject between the heart and the pricked site 91. Accordingly, after performing pricking as described below, the protrusion 110 does not obstruct the flow of blood from the pricked site 91. On the contrary, the protrusion 110 assists the flow of blood from the pricked site 91, because the protrusion 110 presses the portion 94, which is located on the distal side of the pricked site 91.

Figure 10A:
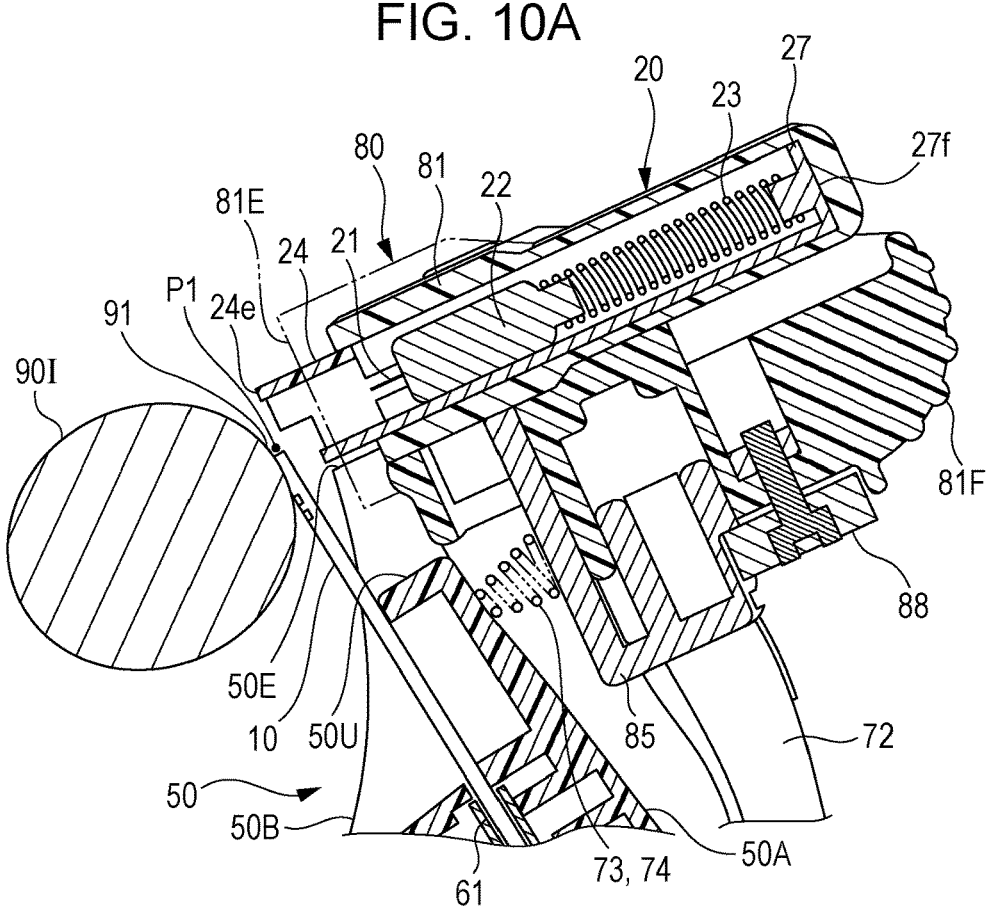
FIG. 10A is a longitudinal sectional view illustrating a state (shown in FIG. 9) before the subject starts pressing a lancet holder with the thumb.

FIG. 10A illustrates a state in which the subject does not substantially apply a force to the end surface 81F of the lancet holder 80. In this state, due to repulsive forces of the conical coil springs 73 and 74 against the front portion 50A of the main body 50, a first end 24e of the lancet device 20 facing the specific position P1 and the end surface 81E of the lancet holder 80 facing the specific position P1 are both separated from the side surface (the pricked site 91) of the index finger 90I.

Figure 10B:
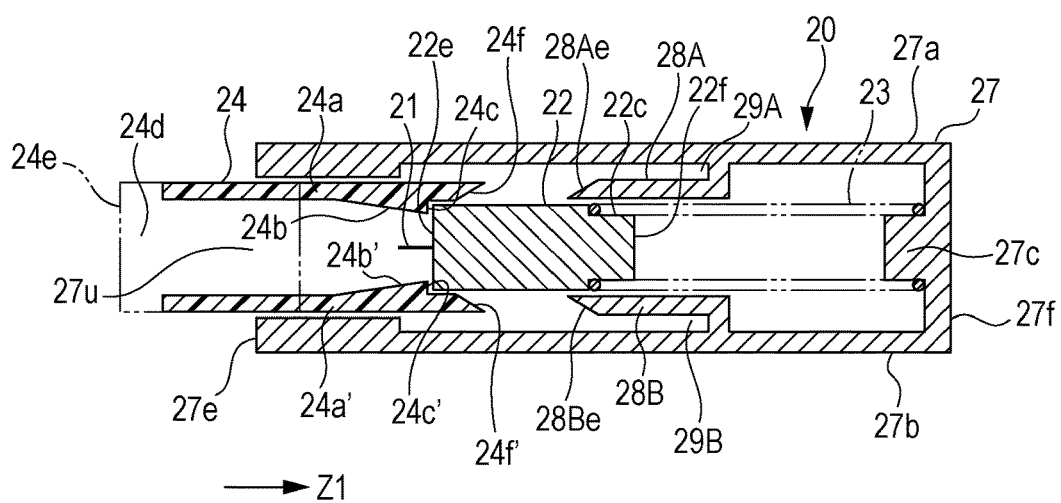
FIG. 10B is a schematic view illustrating the inside of a lancet device in FIG. 10A as viewed from above.

Here, the structure of the lancet device 20 will be described. As illustrated in FIG. 10B, the lancet device 20 includes a guide frame member 27. The guide frame member 27 has an opening 27u on a side thereof near a first end 27e in the longitudinal direction Z1 (horizontal direction in FIG. 10B), the side facing the specific position P1, that is, the pricked site 91. The other sides of the guide frame member 27 are closed. A round bar-shaped portion 27c, which protrudes toward the center of the guide frame member 27 in the longitudinal direction, is formed at a second end 27f of the guide frame member 27.

A mass member 22, which is substantially rectangular-parallelized-shaped, is disposed at substantially the center of the inside of the guide frame member 27 in the longitudinal direction Z1. The lancet 21 is attached to a first end 22e of the mass member 22. A round bar-shaped portion 22c is formed at a second end 22f of the mass member 22.

A cylindrical coil spring 23 is fitted onto and integrally attached to the round bar-shaped portion 22c of the mass member 22 and the round bar-shaped portion 27c of the guide frame member 27. In FIG. 10B, the cylindrical coil spring 23 is not extended or compressed in the longitudinal direction Z1 and is in a free state.

Substantially a half of a movable member 24 is inserted into the opening 27u of the guide frame member 27. The movable member 24 includes a pair of arms 24a and 24a', which extend toward the center of the guide frame member 27 in the longitudinal direction, and a connection plate 24d, which integrally connects the arms 24a and 24a'. A portion of the connection plate 24d near the first end 24e in the longitudinal direction Z1 extends to the outside of the guide frame member 27 so that the portion can come into contact with a portion 95 (see FIG. 9) of the index finger 90I located above the pricked site 91.

The arms 24a and 24a' respectively include inclined portions 24b and 24b' and stepped portions 24c and 24c'. The distance between the inclined portions 24b and 24b' gradually decreases toward second ends 24f and 24f' in the longitudinal direction Z1. The distance between the stepped portions 24c and 24c' is greater than the distance between the inclined portions 24b and 24b'. The second ends 24f and 24f' of the arms 24a and 24a' have tapered surfaces that are inclined in such directions that the distance therebetween increases toward the second end 27f of the guide frame member 27.

A pair of guide portions 28A and 28B are disposed at substantially the center of the guide frame member 27 in the longitudinal direction Z1. The guide portions 28A and 28B extend along the side walls 27a and 27b of the guide frame member 27 in the longitudinal direction Z1, so that the guide portions 28A and 28B can guide the mass member 22. First ends 28Ae and 28Be of the guide portions 28A and 28B in the longitudinal direction Z1 have tapered surfaces that are inclined in such directions that the distance therebetween decreases toward the first end 27e of the guide frame member 27.

Gaps 29A and 29B, into which the second ends 24f and 24f' of the arms 24a and 24a' can be inserted, are respectively formed between the side walls 27a and 27b and the corresponding guide portions 28A and 28B.

Referring back to FIG. 8, as shown in step S13, a subject checks that preparation for measurement has been finished by, for example, seeing that the LED 55A in the front portion 50A of the main body 50 is turned on and off. Because the LED 55A is disposed in a part of the outer surface of the main body 50 against which the subject presses the lancet holder 80 with the thumb 90T, the subject, as a user, can easily see flashing of the LED 55A whole gripping the main body 50 with one hand. Alternatively, the subject may check this before step S12 by seeing a display (such the one shown in FIG. 20) on the LCD 55B, which is disposed in the back portion 50B of the main body 50.

Figure 11A:
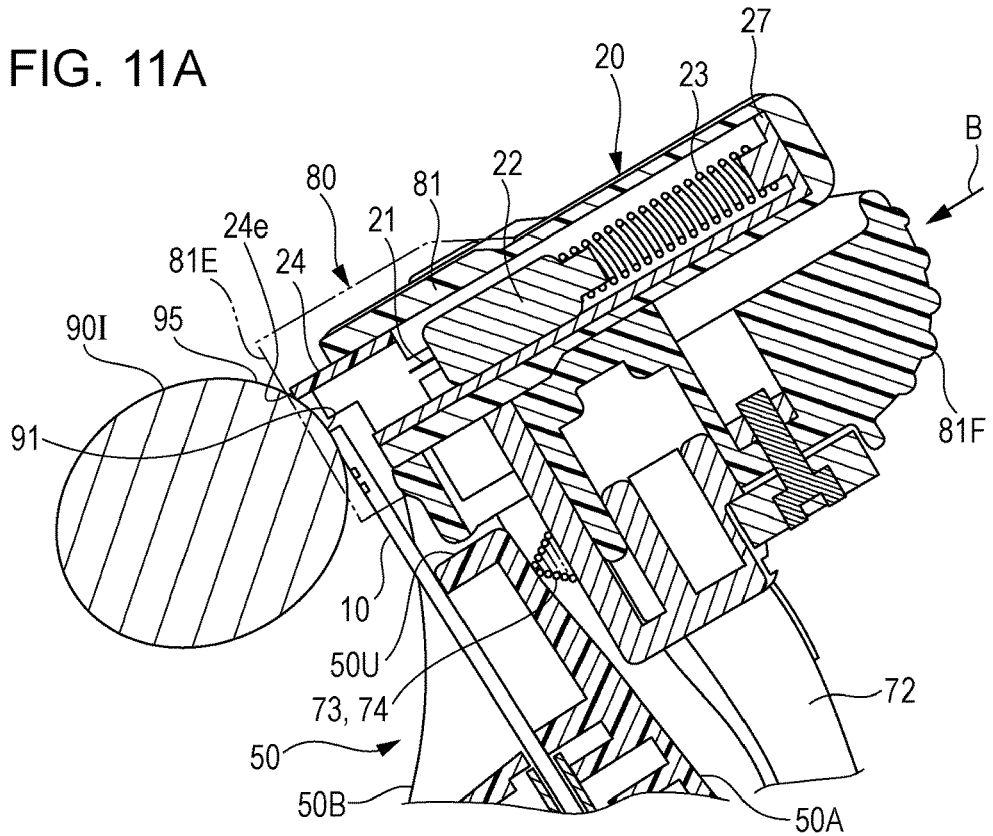
FIG. 11A is a longitudinal sectional view illustrating a state immediately after the subject has started pressing the lancet holder with the thumb.
Figure 11B:
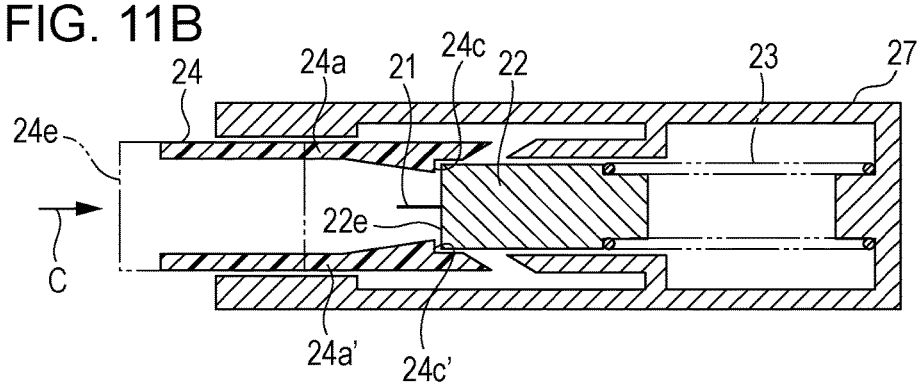
FIG. 11B is a schematic view illustrating the inside of the lancet device in FIG. 11A.
Figure 11C:
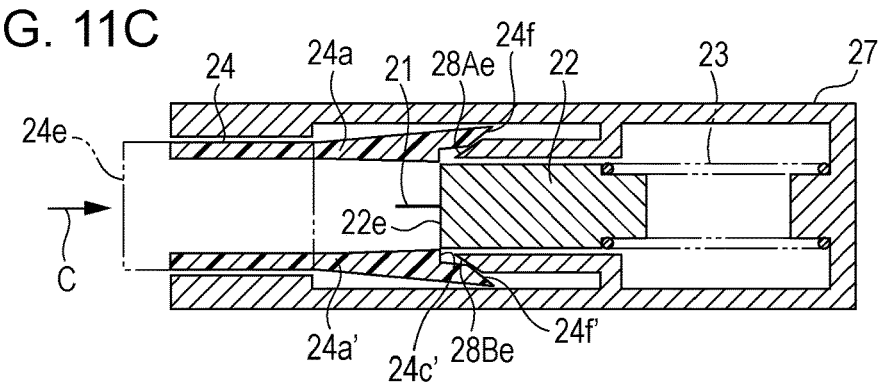
FIG. 11C is a schematic view illustrating the inside of the lancet device at an instant when a mass member, to which a lancet is attached, is removed from a stepped portion of a movable member.
Figure 12A:
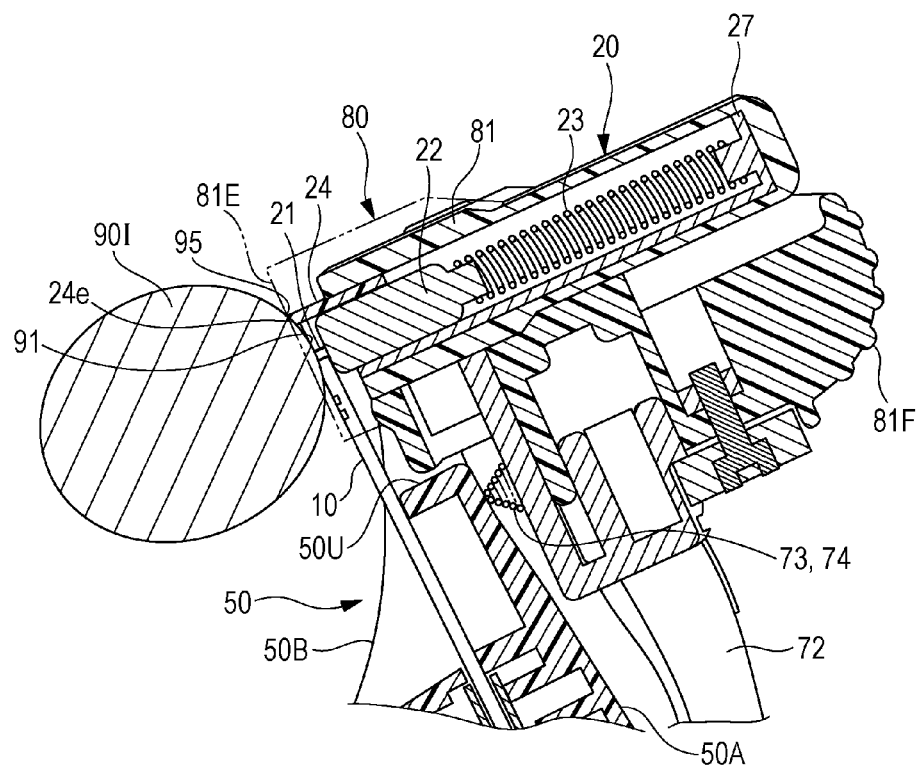
FIG. 12A is a longitudinal sectional view illustrating an instant of pricking.
Figure 12B:
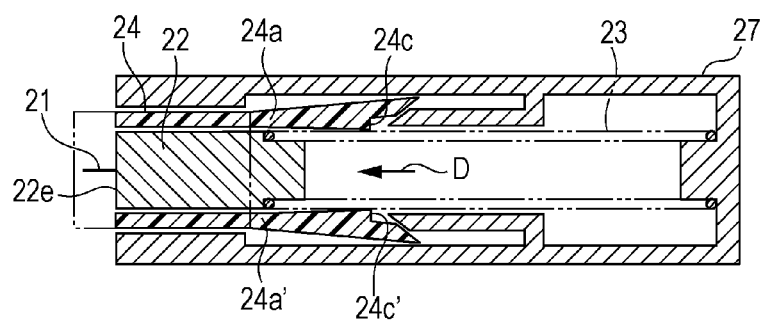
FIG. 12B is a schematic view illustrating the inside of the lancet device in FIG. 12A as viewed from above.
Figure 13A:
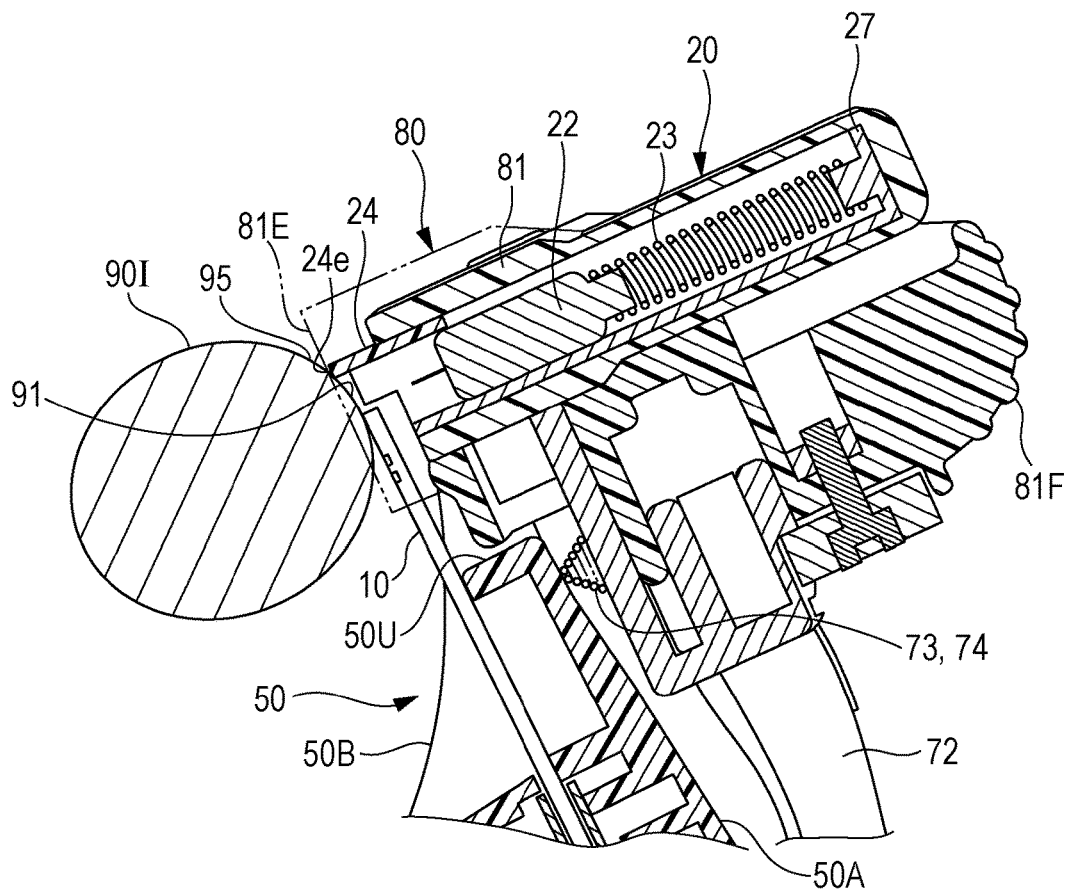
FIG. 13A is a longitudinal sectional view illustrating a state immediately after pricking.
Figure 13B:
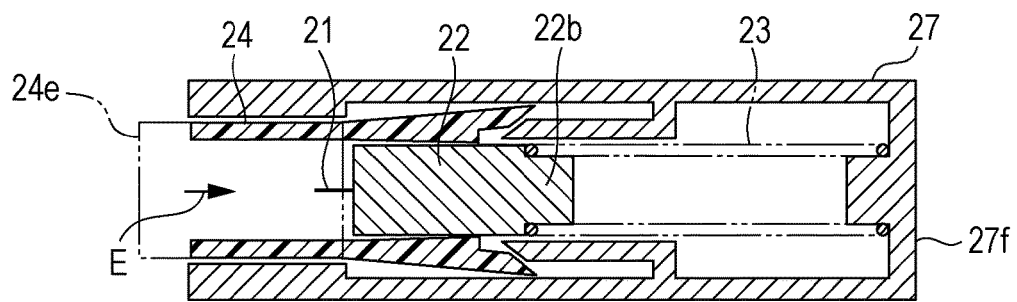
FIG. 13B is a schematic view illustrating the inside of the lancet device in FIG. 13A as viewed from above.

After checking that preparation for measurement has been finished, the subject presses the lancet holder 80 toward the specific position P1 with the thumb 90T to prick the pricked site 91 of the index finger 90I (step S13 shown in FIG. 8). To be specific, as shown by an arrow B in FIG. 11A, the subject presses the lancet holder 80 with the thumb 90T against the repulsive forces of the conical coil springs 73 and 74. Then, the first end 24e of the movable member 24 of the lancet device 20 comes into contact with the portion 95 of the index finger 90I located above the pricked site 91. Thus, as shown by an arrow C in FIG. 11B, the movable member 24 moves into the guide frame member 27 while pushing the mass member 22 with the stepped portions 24c and 24c' against the repulsive force of the cylindrical coil spring 23. As illustrated in FIG. 11C, when the second ends 24f and 24f' of the arms 24a and 24a' of the movable member 24 respectively come into contact with the first ends 28Ae and 28Be of the guide portions 28A and 28B, the second ends 24f and 24f' of the arms 24a and 24a' respectively receive forces in such directions that the second ends 24f and 24f' become separated from each other and enter the gaps 29A and 29B. Thus, the stepped portions 24c and 24c' of the movable member 24 become detached from the first end 22e of the mass member 22. Then, as shown by an arrow D in FIG. 12B, the mass member 22 is pushed by the repulsive force of the cylindrical coil spring 23; and the first end 22e of the mass member 22 and the lancet 21 are ejected from the guide frame member 27 due to inertia. Thus, as illustrated in FIG. 12A, the lancet 21 pricks the pricked site 91 on the side surface of the index finger 90I. Immediately after the pricked site 91 is pricked, as shown by an arrow E in FIG. 13B, the mass member 22 is pulled, together with the lancet 21, into the guide frame member 27 by a tensile force of the cylindrical coil spring 23 and returns a position (initial position) that is substantially at the center of the guide frame member 27. Thus, after pricking has been finished, as illustrated in FIG. 13A, the lancet 21 is held at a position retracted away from the pricked site 91 (the specific position P1) relative to the lancet holder 80.

Figure 14A:
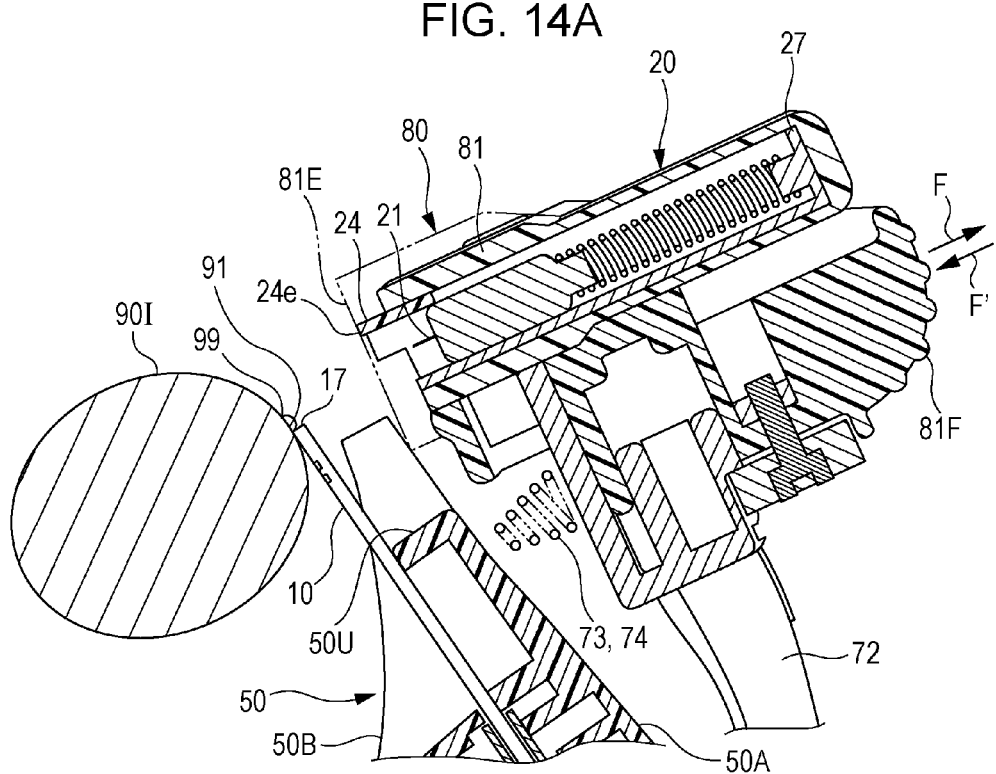
FIG. 14A is a longitudinal sectional view illustrating a state in which pressing with an end surface of the lancet holder is repeatedly performed after pricking.

Subsequently, as shown in step S14 of FIG. 8, the subject separates the thumb 90T from the lancet holder 80 and waits for the end of measurement. At this time, as illustrated in FIG. 14A, due to repulsive forces of the conical coil springs 73 and 74 against the front portion 50A of the main body 50, both the first end 24e of the lancet device 20 facing the specific position P1 and the end surface 81E of the lancet holder 80 facing the specific position P1 become separated from the side surface of the index finger 90I (the pricked site 91). Accordingly, the lancet holder 80 does not obstruct the flow of blood 99, as a bodily fluid, from the pricked site 91.

Because the bodily fluid inlet 17 of the test strip 10 faces the pricked site 91 (the specific position P1), the blood 99 flowing from the pricked site 91 is drawn into the test strip 10 through the bodily fluid inlet 17 of the test strip 10. Then, the measurement circuit of the main body 50 measures the component of the blood 99. When measurement is finished, the LED 55A, which is disposed in the front portion 50A of the main body 50, is continuously turned on. By seeing this, the subject can check that measurement has been finished ("YES" in step S15 in FIG. 8).

If the blood 99 does not easily flow from the pricked site 91 by only pricking the pricked site 91 with the lancet 21, measurement is not finished ("NO" in step S15 in FIG. 8). In this case, the subject, who is gripping the main body 50 with one hand (in this example, the right hand 90R), does not remove the side surface of the index finger 90I (the pricked site 91) from the specific position P1 in the vicinity of the main body 50 (that is, continues to place the side surface of the index finger 90I alongside the main body 50). In this state, as shown by arrows F and F' in FIG. 14A, the subject moves the lancet holder 80, which is an example of a pressing section, back and forth toward the specific position P1 with the thumb 90T against the repulsive forces of the conical coil springs 73 and 74. Thus, the subject repeatedly presses and rubs the portions 92, 93, and 96 (see FIG. 9) adjacent to the pricked site 91 of the index finger 90I (as shown in step S16 in FIG. 8) so as to cause the blood 99 to flow from the pricked site 91. Thus, it is possible to cause the blood 99 to flow from the pricked site 91 without fail. In particular, in this example, the end surface 81E of the lancet holder 80 facing the specific position P1 is frame-shaped so as to surround the lancet 21. Accordingly, when the lancet holder 80 presses the portions 92, 93, and 96 adjacent to the pricked site 91, the lancet holder 80 can push the blood 99 from a region around the pricked site 91 toward the pricked site 91. Thus, it is possible to cause the blood 99 to flow from the pricked site 91 further without fail.

In this example, as illustrated in FIG. 9, the portions 92 and 93, which are located in lateral directions (±Y direction) from the pricked site 91, are directly pressed by the end surface 81E of the lancet holder 80 facing the specific position P1. On the other hand, the portion 96, which is located below the pricked site 91, is indirectly pressed via the test strip 10.

Figure 14B:
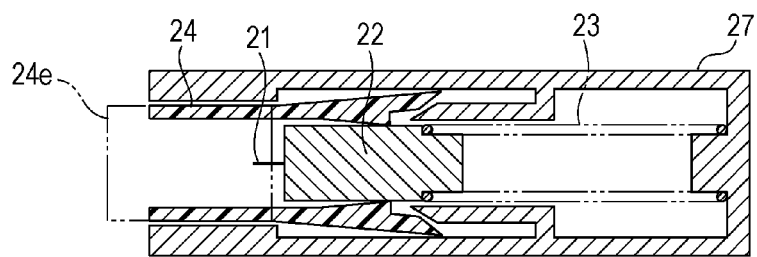
FIG. 14B is a schematic view illustrating the inside of the lancet device shown in FIG. 14A as viewed from above.

Even while repeatedly pressing the pricked site 91 as illustrated in FIG. 14A, if the subject stops applying a force to the lancet holder 80 with the thumb 90T (or reduces the force) in order to check whether blood is flowing from the pricked site 91, the lancet holder 80 returns to a position (initial position) that is separated from the specific position P1, and the pricked site 91 of the index finger 90I and the vicinity of the pricked site 91 are released. Accordingly, the lancet holder 80 does not obstruct the flow of the blood 99 from the pricked site 91. After pricking has been finished, as illustrated in FIGS. 14A and 14B, the lancet 21 is pulled into the guide frame member 27 and held at a position away from the pricked site 91 (the specific position P1) relative to the lancet holder 80. Accordingly, the subject can repeat pressing without repeating pricking. Thus, it is possible to cause the blood 99 to flow from the pricked site 91 without fail and without giving an unnecessary pain to the subject.

As described above, the blood 99 from the pricked site 91 flows through the bodily fluid inlet 17 of the test strip 10 and is applied to (the sensor portion 15 of) the test strip 10. Accordingly, measurement can be smoothly and accurately performed.

When measurement is finished in this way ("YES" in step S15 in FIG. 8), the subject checks the blood glucose level by seeing the LCD 55B disposed in the back portion 50B of the main body 50 (step S17 in FIG. 8). Subsequently, the subject removes the lancet device 20 from the lancet holder 80 and discards the lancet device 20, and removes the test strip 10 from the main body 50 and discards the test strip 10 (step S18 in FIG. 8).

As described above, with the bodily-fluid-component analyzing apparatus 1, a subject can obtain a blood sample by pricking the pricked site 91 while gripping the main body 50 with one hand and by moving the lancet holder 80 relative to the main body 50 along a predetermined movement path with the thumb 90T of the one hand. That is, the subject can perform the operation for obtaining a blood sample with one hand. Moreover, because the thumb 90T of a hand can generally generate a larger force than other fingers, the subject can easily perform the operation of obtaining a blood sample. In particular, in this example, the index finger 90I, which is a specific finger of one hand other than the thumb 90T, is placed at the specific position P1 in the vicinity of the main body 50, so that the blood 99 is obtained from the pricked site 91 of the index finger 90I. That is, the subject can perform the whole process of obtaining a blood sample with one hand.

If it is still difficult for the subject to cause the blood 99 flow from the pricked site 91 even by repeatedly pressing the lancet holder 80 against the portion adjacent to the pricked site 91, the subject may perform an operation of temporarily removing the pricked site 91 from the specific position P1 in the vicinity of the main body 50 and rubbing a portion around the pricked site 91 with a hand to cause the blood 99 flow from the pricked site 91. Then, the subject may apply the blood 99 to the bodily fluid inlet 17 of the test strip 10. (In this case, however, the sample of the blood 99 may become contaminated or the component of the blood 99 may be changed due to evaporation of water in the blood 99.)

First Modified Embodiment

Figure 15A:
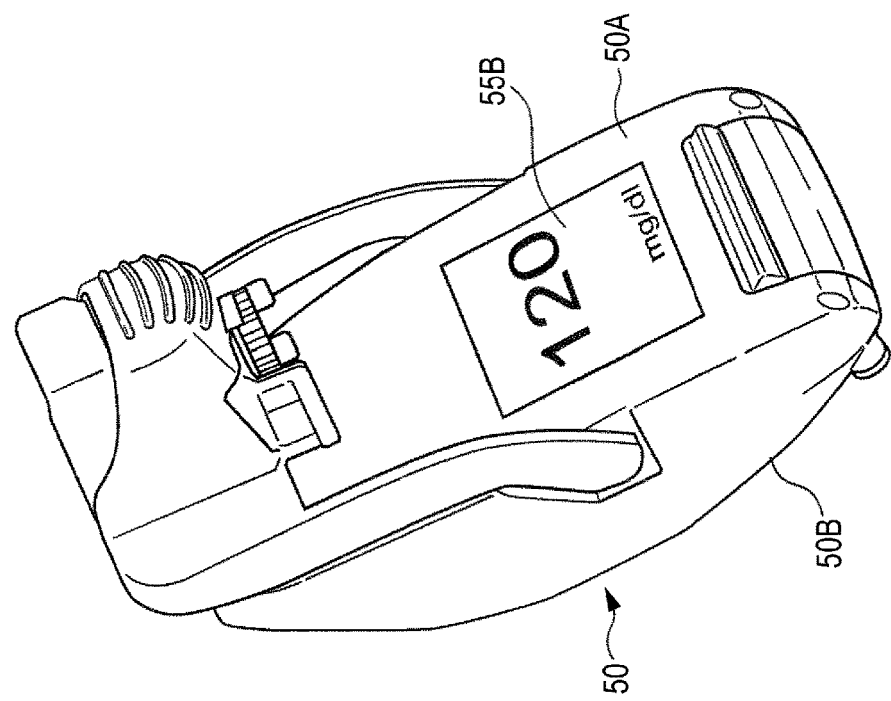
FIG. 15A illustrates an example in which an LED is disposed in a front portion of the main body.
Figure 15B:
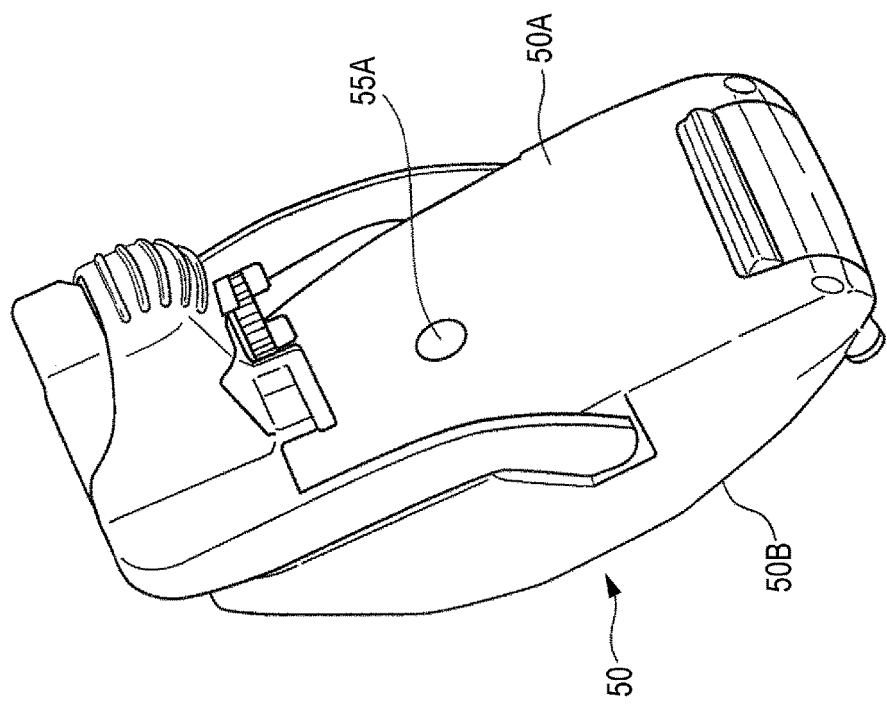
FIG. 15B illustrates an example in which an LCD is disposed in a front portion of the main body.

In the example described above, as illustrated in FIG. 15A, the indicator 55 includes the LED 55A, which is disposed in the front portion 50A of the main body 50, and the LCD 55B, which is disposed in the back portion 50B of the main body 50. However, this is not a limitation. As illustrated in FIG. 15B, the LED 55A may be omitted, and only the LCD 55B may be disposed in the front portion 50A of the main body 50. In this case, the LCD 55B displays, for example, a measurement status as shown in FIG. 20, a measurement result shown in FIG. 15B (in this example, a blood glucose level of 120 mg/dL), and other information.

Second Modified Embodiment

Figure 16B:
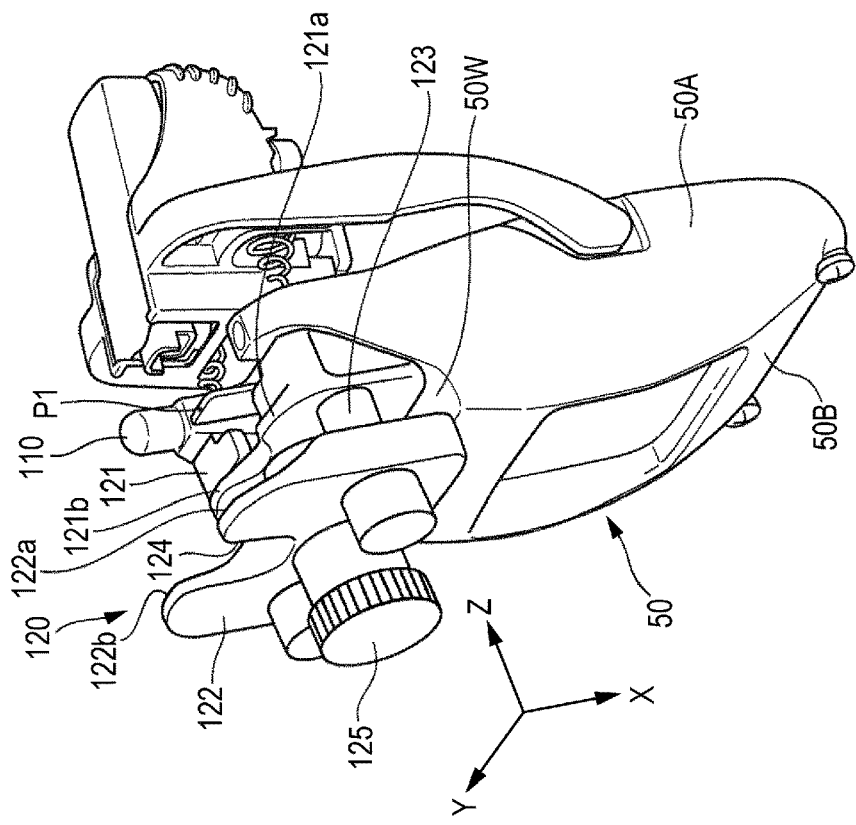
FIGS. 16A and 16B illustrate an example in which a positioning mechanism is disposed in a recess in a back portion of the main body.
Figure 16A:
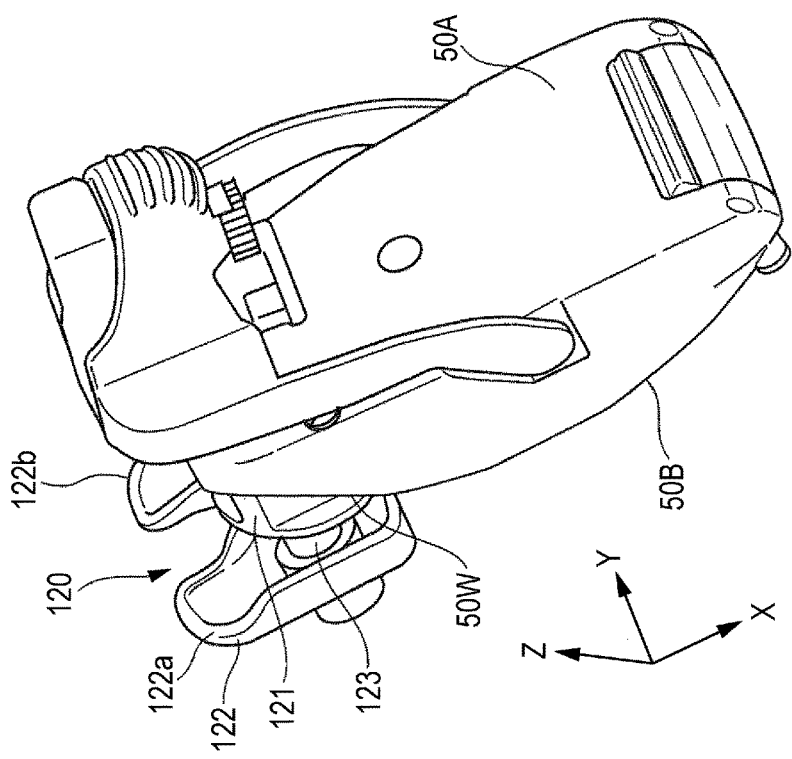

In the example described above, the protrusion 110 is used as a positioning element for positioning the pricked site 91 at the specific position P1 in the vicinity of the main body 50. However, this is not a limitation. For example, a positioning mechanism 120 shown in FIGS. 16A and 16B may be used. (FIG. 16A and FIG. 16B are respectively a front perspective view and a rear perspective view corresponding to FIG. 1 and FIG. 2.) The positioning mechanism 120 includes a fixing member 121, a pair of guide bars 123 and 124, a rear member 122, and a setting screw 125. The fixing member 121 is disposed along the recess 50W in the back portion 50B of the main body 50. The guide bars 123 and 124 extend parallel to each other from the fixing member 121 toward the back side (in the −Z direction). The rear member 122 is attached to the guide bars 123 and 124 so as to be slidable in the Z direction along the guide bars 123 and 124. The setting screw 125 is used to set the distance between the fixing member 121 and the rear member 122 in the Z direction. The positioning mechanism 120 is removably attached to the back portion 50B of the main body 50 by fitting a pair of protrusions (not shown) of the fixing member 121 into the holes W1 and W2 shown in FIG. 2.

Two semicircular bulges 121a and 121b, which are to come into contact with the ball of the index finger 90I of a hand (the left hand or the right hand) of a subject, are formed in an upper part of the fixing member 121. The bulges 121a and 121b restrict displacement of the index finger 90I in a downward direction (the +X direction). Displacement of the index finger 90I in an upward direction (in the −X direction) does not usually occur owing to the structure of the finger. As a result, the index finger 90I is positioned in the X direction.

Upper parts of the rear member 122 facing the back portion 50B of the main body 50 (on the +Z side) have edges 122a and 122b, which protrude in the +Z direction and which are curved along a side surface of the index finger 90I (a side surface opposite to a side surface including the pricked site 91).

The setting screw 125 extends through the rear member 122 in the Z direction and is screwed into a female thread (not shown) formed in a back portion (−Z side) of the fixing member 121. The subject can set the positions of the edges 122a and 122b of the rear member 122 in the Z direction (the distances from the specific position P1) by rotating the setting screw 125 and sliding the rear member 122 along the guide bars 123 and 124 in the Z direction. The edges 122a and 122b, whose positions have been set, restrict displacement of the index finger 90I in the −Z direction by coming into contact with a side surface of the index finger 90I opposite to a side surface including the pricked site 91. Moreover, the aforementioned protrusion 110 restricts displacement of the index finger 90I in the +Z direction. As a result, the index finger 90I is positioned in the Z direction.

Thus, the positioning mechanism 120 positions the index finger 90I in the X direction and in the Z direction. (Note that displacement of the index finger 90I in the Y direction does not cause a serious problem.) Accordingly, the subject can place the pricked site 91 of the index finger 90I accurately at the specific position P1 in the vicinity of the main body 50.

Moreover, in the positioning mechanism 120, the bulges 121a and 121b of the fixing member 121 and the edges 122a and 122b of the rear member 122, which come into contact with the index finger 90I, are disposed so as to correspond to a portion of the subject that is outside of a blood flow path between the heart and the pricked site 91 (such as the ball of the index finger 90I or a side surface of the index finger 90I opposite to a side surface including the pricked site 91). Furthermore, the area over which the positioning mechanism 120 comes into contact with the index finger 90I is comparatively small. Accordingly, the positioning mechanism 120 does not obstruct the flow of the blood 99 from the pricked site 91.

Third Modified Embodiment

Instead of the positioning mechanism 120 described above, a positioning mechanism 130 illustrated in FIGS. 17A and 17B may be used. (FIG. 17A and FIG. 17B are respectively a front perspective view and a rear perspective view corresponding to FIG. 1 and FIG. 2.)

The positioning mechanism 130 includes a fixing member 131 and a rear member 132. The fixing member 131 is disposed along the recess 50W in the back portion 50B of the main body 50. The rear member 132 is attached to the back side (the −Z side) of the fixing member 131. The positioning mechanism 130 is removably attached to the back portion 50B of the main body 50 by fitting a pair of protrusions (not shown) of the fixing member 131 into the holes W1 and W2 shown in FIG. 2.

Two semicircular bulges 131a and 131b, which are to come into contact with the ball of the index finger 90I of a hand (the left hand or the right hand) of a subject, are formed in an upper part the fixing member 131. As with the second modified embodiment, the bulges 131a and 131b position the index finger 90I in the X direction.

The rear member 132 includes a cylindrical portion 132b and a spiral portion 132a, which is integrally and continuously formed with the back side (−Z side) of the cylindrical portion 132b. The cylindrical portion 132b is fitted onto a cylindrical bar (not shown) formed on the back side (−Z side) of the fixing member 131 so as to be rotatable, as indicated by an arrow R1, around an axis 133 extending in the Z direction. The spiral portion 132a has an inclined surface (spiral surface) that is inclined at an angle of about 45° with respect to the axis 133. With this structure, by rotating the rear member 132 around the axis 133, the subject can set the position of a portion 132x of the spiral portion 132a of the rear member 132, which is located above the cylindrical portion 132b (the distance from the specific position P1), in the Z direction. The portion 132x, whose position has been set, restricts displacement of the index finger 90I in the −Z direction by coming into contact with a side surface of the index finger 90I opposite to a side surface including the pricked site 91. Moreover, the aforementioned protrusion 110 restricts displacement of the index finger 90I in the +Z direction. As a result, the index finger 90I is positioned in the Z direction.

Thus, the positioning mechanism 130 positions the index finger 90I in the X direction and in the Z direction as the aforementioned positioning mechanism 120 does. (Note that displacement of the index finger 90I in the Y direction does not cause a serious problem.) Accordingly, the subject can place the pricked site 91 of the index finger 90I accurately at the specific position P1 in the vicinity of the main body 50.

Moreover, the positioning mechanism 130, which includes only two members 131 and 132, has a simple structure.

Fourth Modified Embodiment

If it is not necessary to restrict displacement of the index finger 90I in the −Z direction, a positioning member 140 illustrated in FIGS. 18A and 18B may be used. (FIG. 18A and FIG. 18B are respectively a front perspective view and a rear perspective view corresponding to FIG. 1 and FIG. 2.)

The positioning member 140 corresponds to the fixing members 121 and 131 of the positioning mechanisms 120 and 130 described above. The positioning member 140 is removably attached to the back portion 50B of the main body 50 by fitting a pair of protrusions (not shown) of the positioning member 140 into the holes W1 and W2 shown in FIG. 2.

Two semicircular bulges 141a and 141b, which are to come into contact with the ball of the index finger 90I of a hand (the left hand or the right hand) of a subject, are formed in an upper part the positioning member 140. As with the second and third modified embodiments, the bulges 141a and 141b position the index finger 90I in the X direction. Moreover, the aforementioned protrusion 110 restricts displacement of the index finger 90I in the +Z direction.

The positioning member 140 has a simpler structure than the positioning members of the second and third modified embodiments.

Fifth Modified Embodiment

In the example shown in FIG. 9, a subject grips the main body 50 with (only) one hand. However, this is not a limitation. For example, as illustrated in FIGS. 19A and 19B, a bottom element 150, which is used to place the main body 50 on a flat surface 200, may be attached to the main body 50, and the main body 50 may be supported by the flat surface 200.

The bottom element 150 includes a receiving surface 150*a*, which is curved along the back portion 50B of the main body 50, and a bottom surface 150*b*, which is flat so as to be placed along the flat surface 200. The bottom element 150 is removably attached to the main body 50 by fitting a protrusion (not shown), which is formed on the receiving surface 150*a*, into a recess in the LCD 55B (see FIG. 2), which is disposed in the back portion 50B of the main body 50.

In this example, the main body 50 is placed on the flat surface 200 via the bottom element 150. The specific position P1, at which the pricked site 91 is to be placed in the vicinity of the main body 50, is substantially at the same height as the index finger 90I of a hand that is placed on the flat surface 200. Accordingly, a subject can place a side surface of the index finger 90I (the pricked site 91) of a hand at the specific position P1 by placing the hand on the flat surface 200 and extending the hand along the main body 50. In this case, both the main body 50 and the hand are stably supported by the flat surface 200. Accordingly, the subject can easily perform the operation of obtaining a sample of the blood 99.

The LCD 55B may be disposed in the front portion 50A of the main body 50, and the bottom element 150 may be integrally attached to the main body 50.

In the embodiments described above, the end surface 81E of the lancet holder 80, which is an example of a pressing section and which faces the specific position P1, has an angular U-shape that opens upward. However, this is not a limitation. The end surface 81E of the lancet holder 80, which is an example of a pressing section, facing the specific position P1 may have, for example, a rectangular frame-like shape so that the blood 99 in the living body can be pushed from a region around the pricked site 91 toward the pricked site 91. Thus, it is possible to cause the blood 99 to flow from the pricked site 91 further without fail.

In the embodiments described above, blood glucose is measured as a specific component in the blood. However, this is not a limitation. It is possible to measure the concentrations of cholesterol and lactic acid in the blood by appropriately selecting the material of the reagent layer of the sensor portion 15 from known materials. A bodily fluid other than blood may be measured.

In the embodiments described above, the pricked site is a part of a side surface of the index finger of a hand. However, this is not a limitation. The pricked site may be a part of a finger other than the index finger or may be a part of palm or arm.

A program for measuring the component of a living body, which is stored in the memory 54, may be encoded in a non-transitory computer-readable storage medium (a memory, a hard disk drive, or an optical disc), and a general-purpose computer may perform the measurement method described above.

In the embodiments described above, the bodily-fluid-component analyzing apparatus 1 is a standalone apparatus. However, this is not a limitation. The main body 50 may include a communication unit. The communication unit sends information representing a measurement result (the blood glucose level) obtained by the CPU 53 through a network and receives information from an external apparatus through a network and transfers the information to the controller. Thus, for example, a subject can receive an advice or other information from a doctor through a network. The communication through the network may be wireless or wired.

The embodiments described above are examples and may be modified in various ways within the sprit and scope of the present invention. Although the embodiments described above can be used independently, the embodiments may be used in combination. Various features of the embodiments, each of which can be used independently, may be used in combination with other features of other embodiment.

What is claimed is:

1. An integrated bodily-fluid-component analyzing apparatus that obtains a sample of a bodily fluid by pricking a living body with a lancet and measures a component of the sample of the bodily fluid, the apparatus comprising:
    a main body;
    a lancet holder that is connected to the main body so as to be movable back and forth along a predetermined movement path relative to the main body;
    a guide movably connecting the main body and the lancet holder, wherein the guide is configured to move the lancet holder in relation to the main body between a pressing position at which a surface of the lancet holder presses a portion of the living body adjacent to a pricked site and a retracted position at which the surface of the lancet holder is separated away from the living body adjacent to the pricked site;
    an elastic member configured to urge the lancet holder in a direction away from the specific position relative to the main body;
    a lancet that is removably attached to the lancet holder; and
    a test strip that is removably attached to the main body by a connector and that is used to measure the component of the bodily fluid flowing from a pricked site of the living body pricked with the lancet, wherein the connector holds the test strip still at a predetermined position relative to the main body before, during, and after the movement of the lancet holder between the pressing position and the retracted position,
    wherein the movement path of the lancet holder and a bodily fluid inlet of the test strip face a specific position that is in a vicinity of the main body and at which the pricked site of the living body is to be placed, and wherein the surface of the lancet holder is configured to press a portion of the living body adjacent to the pricked site so as to cause the bodily fluid to flow from the pricked site.

2. The bodily-fluid-component analyzing apparatus according to claim 1, wherein the surface configured to press a portion of the living body is an end surface of the lancet holder facing the specific position.

3. The bodily-fluid-component analyzing apparatus according to claim 2, wherein the end surface of the lancet holder facing the specific position surrounds a portion of the lancet.

4. The bodily-fluid-component analyzing apparatus according to claim 2, further comprising:

a biasing element that keeps the lancet retracted in a direction away from the specific position relative to the main body after the lancet has pricked the pricked site of the living body.

5. The bodily-fluid-component analyzing apparatus according to claim 1, further comprising:
a protrusion configured to position the pricked site of the living body at the specific position,
wherein the protrusion is disposed so as to correspond to a portion of the living body that is outside a blood flow path between a heart and the pricked site of the living body.

6. The bodily-fluid-component analyzing apparatus according to claim 5,
wherein the protrusion is attachable to and removable from the main body.

7. The bodily-fluid-component analyzing apparatus according to claim 5,
wherein the protrusion comes into contact with a portion of the living body located on a distal side of the pricked site.

8. The bodily-fluid-component analyzing apparatus according to claim 1,
wherein the main body is sized so as to allow a subject, as the living body, to grip the main body with one hand, and
wherein the lancet holder is disposed so as to be moved by a thumb of the one hand along the predetermined path relative to the main body.

9. The bodily-fluid-component analyzing apparatus according to claim 8,
wherein, when the subject grips the main body with one hand and the thumb of the one hand is in contact with the lancet holder, a specific finger of the one hand other than the thumb is placed at the specific position in the vicinity of the main body.

10. The bodily-fluid-component analyzing apparatus according to claim 8,
wherein the main body includes a measurement circuit for measuring the component of the bodily fluid by using the test strip, and
wherein an indicator, which indicates a status or a result of measurement of the component of the bodily fluid performed by the measurement circuit, is disposed on a part of an outer surface of the main body toward which the lancet holder is to be pressed by the thumb.

11. The bodily-fluid-component analyzing apparatus according to claim 1, further comprising:
a bottom element that allows the main body to be placed on a flat surface and that is removably attached to or integrated with the main body,
wherein, when the main body is placed on the flat surface via the bottom element, the specific position, which is in the vicinity of the main body and at which the pricked site of the living body is to be placed, is at the same height from the flat surface as a specific finger of a hand that is placed on the flat surface.

* * * * *